(12) United States Patent
Lee et al.

(10) Patent No.: US 10,982,262 B2
(45) Date of Patent: Apr. 20, 2021

(54) QUENCHER AND USE THEREOF

(71) Applicant: SFC CO., LTD., Cheongju-si (KR)

(72) Inventors: Do-Min Lee, Asan-si (KR); Seung-Soo Lee, Daejeon (KR); Jin-Hee Park, Yongin-si (KR); Sun-Ho Kim, Yongin-si (KR); Goutam Masanta, Cheongju-si (KR); Jong-Tae Je, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 342 days.

(21) Appl. No.: 16/199,050

(22) Filed: Nov. 23, 2018

(65) Prior Publication Data
US 2019/0194730 A1     Jun. 27, 2019

(30) Foreign Application Priority Data

Nov. 28, 2017  (KR) .......................... 10-2017-0160117
Sep. 28, 2018  (KR) .......................... 10-2018-0115761

(51) Int. Cl.
| | | |
|---|---|---|
| C09B 11/00 | (2006.01) |
| C09B 11/08 | (2006.01) |
| C09B 11/24 | (2006.01) |
| C12Q 1/68 | (2018.01) |
| C12Q 1/6818 | (2018.01) |
| C07D 513/06 | (2006.01) |

(52) U.S. Cl.
CPC .......... *C12Q 1/6818* (2013.01); *C07D 513/06* (2013.01); *C09B 11/00* (2013.01); *C09B 11/08* (2013.01); *C09B 11/24* (2013.01)

(58) Field of Classification Search
CPC ......... C09B 11/00; C09B 11/08; C09B 11/24; C12Q 1/6818
See application file for complete search history.

*Primary Examiner* — Jezia Riley
(74) *Attorney, Agent, or Firm* — Studebaker & Brackett PC

(57) ABSTRACT

The present invention relates to a quencher having a quenching effect on a fluorescent material exhibiting luminescence characteristics at an excited energy level, and various uses thereof.

15 Claims, 5 Drawing Sheets

Specification includes a Sequence Listing.

QUENCHER AND USE THEREOF

CROSS-REFERENCE TO RELATED APPLICATIONS

This application claims the priority of Korean Patent Application No. 10-2017-0160117 filed on Nov. 28, 2017 and No. 10-2018-0115761 filed on Sep. 28, 2018 in the Korean Intellectual Property Office, the disclosure of which is hereby incorporated by reference in its entirety.

TECHNICAL FIELD

The present invention relates to a quencher having a quenching effect on a fluorescent material exhibiting luminescence characteristics at an excited energy level, and various uses thereof.

This research was supported by a grant from the Advanced Technology Center (ATC) Program (Ser. No. 10/076,988, Development of fluorescent materials and their application technologies for molecular diagnosis) funded by the Ministry of Trade, Industry & Energy of the Republic of Korea.

BACKGROUND ART

A quencher means a molecule capable of quenching the fluorescence of a fluorescent molecule, and a dye having a property capable of absorbing light is generally used.

Mechanisms of quenching phenomenon are known to occur through aggregation of dyes such as fluorescence resonance energy transfer (FRET), photo-induced electron transfer and formation of H-dimer.

When a quencher is used to control or quench the fluorescence of the fluorescent dye, it is most important that the range of the absorption wavelength of the quenching dye covers (overlaps) a substantial part or all of the wavelength region of the fluorescent light represented by the fluorescent dye.

In order to obtain a quenching effect, the length between the fluorescent dye and the quencher is also important. For example, the number of bases in the case of DNA and the number of amino acids in the case of peptide/protein are considered. The length of the linker to which the fluorescent dye and the quencher are labeled may be adjusted to achieve a higher quenching effect.

In the case of a quencher used commercially in the field of biotechnology, a combination of fluorescence-fluorescent dyes utilizing FRET phenomenon has been widely used, although a dye structure which cannot emit but only absorb light is generally selected. Such combined fluorescence-extinction and fluorescence-fluorescent dyes are able to impart a kind of on/off function of fluorescence because the original fluorescence thereof is either restored or strengthened when the distances between the fluorescence-extinction and fluorescence-fluorescent dyes recede from each other or biomolecules are separated from each other. These properties have been widely used in designing biosensors or activation probes capable of responding to biomarkers such as specific proteins/enzymes.

Fluorescent or quenching dyes used in the biotechnology field are limited to only FDA-approved dyes, such as indocyanine green or methylene blue, and generally have reactive groups capable of binding to the substituents of biomolecules. Although a variety of the reactive groups have been known, they have been verified for a long time by researchers with respect to a high degree of substituent selectivity, reaction rate, yield, reproducibility and stability. In recent years, the reactive groups introduced into dyes for practical research or commercial purposes have been limited to several types.

For example, the most frequently used reactive groups for binding with amine groups of protein molecules are succinimidyl ester and isothiocyanate, and the most reactive groups for binding with thiol groups of protein molecules are maleimide. Dichlorotriazine is mainly used as the reactive group for binding with a hydroxy group of a protein molecule.

However, most of the reactive groups are difficult to maintain a long-term reaction and storage stability under water-soluble condition or in a substitution reaction.

DETAILED DESCRIPTION OF THE INVENTION

Technical Problem

It is an object of the present invention to provide a novel quencher as a compound that can be widely used for observing the identification of biomolecules in the field of optical imaging.

Further, it is another object of the present invention to provide an oligonucleotide, a composition and a support for detecting a nucleic acid comprising the above novel quencher, and a method for detecting the nucleic acid.

Technical Solution

According to one aspect of the present invention for solving the above technical problem, there is provided a quencher represented by formula 1 or 2 as follows:

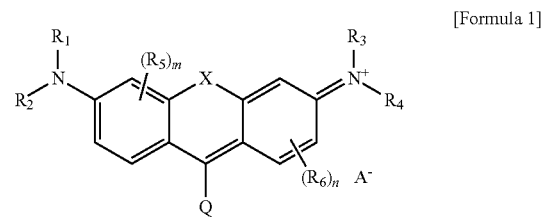

[Formula 1]

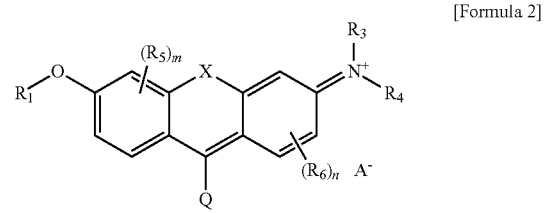

[Formula 2]

wherein Q is represented by Formula (3)

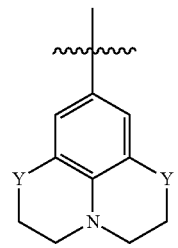

or Formula (4)

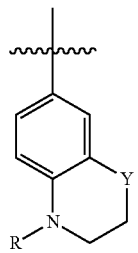

or Formula (4)

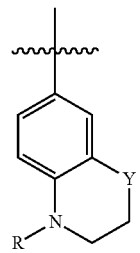

$R_1$, $R_2$, $R_3$, $R_4$, $R_5$, $R_6$ and R are each independently selected from hydrogen, deuterium, electron donating group and electron withdrawing group, m and n are each independently an integer of 0 to 3, X is O, S, $CR_7R_8$ or $SiR_7R_8$, Y is O or S, $R_7$ and $R_8$ are each independently selected from substituted or unsubstituted $C_1$-$C_{40}$ alkyl, substituted or unsubstituted $C_1$-$C_{40}$ heteroalkyl including at least one heteroatom, substituted or unsubstituted aryl, and substituted or unsubstituted heteroaryl, or are combined with each other to form a ring, and at least one of $R_1$, $R_2$, $R_3$ and $R_4$ is a functional group selected from the group consisting of a carboxyl, a carboxyl derivative, a hydroxyl, a haloalkyl, a nucleophile, an aldehyde, a ketone, a sulfonyl halide, a thiol, an amine, a sulfhydryl, an alkene, an epoxide and a phospoamidite, or is a reactive group capable of covalently bonding to the functional group.

Further, according to another aspect of the present invention, there is provided a quencher represented by the following formula (5) or (6):

[Formula 5]

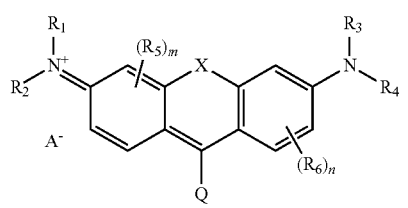

[Formula 6]

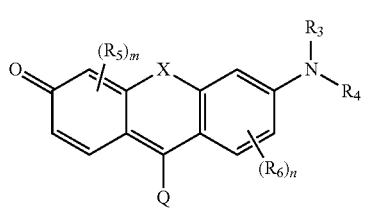

wherein Q is represented by Formula (3)

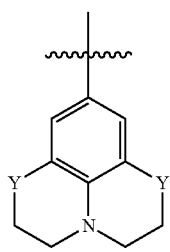

$R_1$, $R_2$, $R_3$, $R_4$, $R_5$, $R_6$ and R are each independently selected from hydrogen, deuterium, electron donating group and electron withdrawing group, m and n are each independently an integer of 0 to 3, X is O, S, $CR_7R_8$ or $SiR_7R_8$, Y is O or S, $R_7$ and $R_8$ are each independently selected from substituted or unsubstituted $C_1$-$C_{40}$ alkyl, substituted or unsubstituted $C_1$-$C_{40}$ heteroalkyl including at least one heteroatom, substituted or unsubstituted aryl, and substituted or unsubstituted heteroaryl, or are combined with each other to form a ring, and at least one of $R_1$, $R_2$, $R_3$ and $R_4$ is a functional group selected from the group consisting of a carboxyl, a carboxyl derivative, a hydroxyl, a haloalkyl, a nucleophile, an aldehyde, a ketone, a sulfonyl halide, a thiol, an amine, a sulfhydryl, an alkene, an epoxide and a phosphoramidite, or is a reactive group capable of covalently bonding to the functional group.

Further, according to another aspect of the present invention, there is provided an oligonucleotide including the above quencher, a minor groove binder (MGB), and a fluorophore.

Further, according to still another aspect of the present invention, there is provided a composition for detecting a nucleic acid comprising the above oligonucleotide.

Further, according to still another aspect of the present invention, there is also provided a support for detecting a nucleic acid comprising the above quencher, a support, and a linker connecting the quencher and the support.

Furthermore, according to another aspect of the present invention, there is provided a method for detecting a nucleic acid, comprising: (a) preparing a reaction mixture including a target nucleic acid, a reagent necessary for amplifying the target nucleic acid and an oligonucleotide, (b) amplifying the target nucleic acid in the reaction mixture by a polymerase chain reaction, and (c) measuring fluorescence intensity of the reaction mixture.

Effects of the Invention

The present invention is directed to a quencher having a quenching effect on a fluorescent material exhibiting luminescence characteristics at an excited energy level, and a variety of uses thereof, and the quencher according to the present invention can exhibit excellent quenching characteristics as the quenching efficiency is higher than that of the conventional quencher.

DETAILED DESCRIPTION OF EMBODIMENTS

Figure 1:
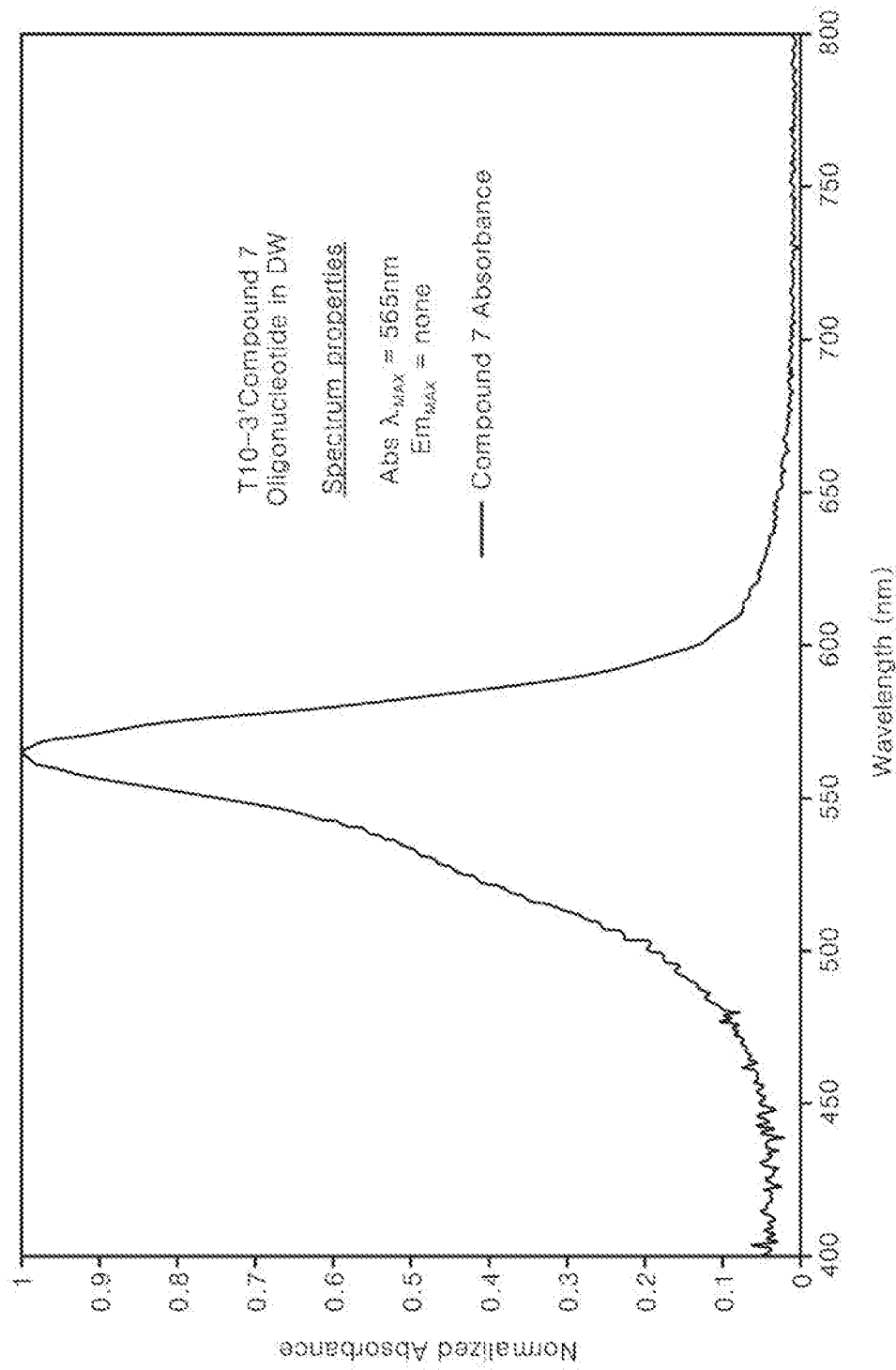
FIG. 1 shows an absorption spectrum of a quencher according to various embodiments of the present invention.

In order to facilitate a better understanding of the present invention, certain terms are defined herein for the purpose of convenience. Unless otherwise defined herein, the scientific and technical terms used herein may have the meaning as commonly appreciated by a person who has an ordinary knowledge in the relevant art.

Also, unless the context clearly indicates otherwise, the singular form of term may refer to plural forms thereof, and the plural forms of the term may mean the singular form thereof.

New Quencher

According to one aspect of the present invention, there is provided a quencher represented by Formula 1 or 2 as follows:

[Formula 1]

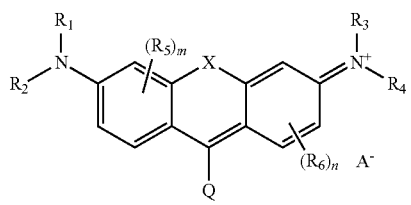

[Formula 2]

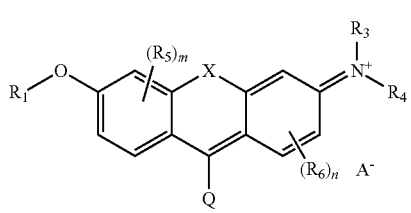

Further, according to another aspect of the present invention, there is provided a quencher represented by the following formula (5) or (6):

[Formula 5]

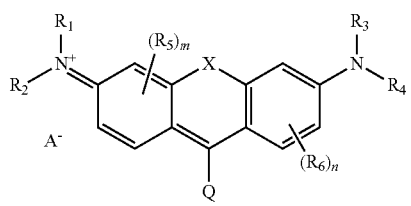

[Formula 6]

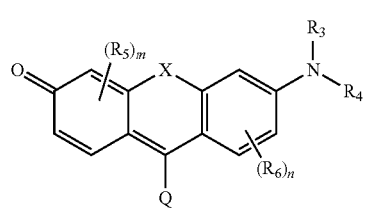

wherein Q is represented by Formula (3)

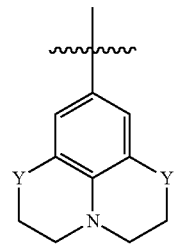

or Formula (4)

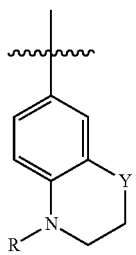

$R_1$, $R_2$, $R_3$, $R_4$, $R_5$, $R_6$ and R are each independently selected from hydrogen, deuterium, electron donating group and electron withdrawing group, wherein the quencher represented by the formula (2) and the quencher represented by the formula (6) are resonance structures that may be interconverted according to pH.

Here, the electron donating group refers to a functional group which tends to push electrons through a triggering effect or a resonance effect, and may be, for example, substituted or unsubstituted $C_1$-$C_{40}$ alkyl, substituted or unsubstituted $C_1$-$C_{40}$ heteroalkyl including at least one heteroatom, substituted or unsubstituted $C_2$-$C_{40}$ alkenyl, substituted or unsubstituted $C_2$-$C_{40}$ alkynyl, substituted or unsubstituted $C_1$-$C_{40}$ alkoxy, substituted or unsubstituted aryloxy, substituted or unsubstituted thiol group, substituted or unsubstituted $C_1$-$C_{40}$ alkylthio, substituted or unsubstituted arylthio, hydroxy, substituted or unsubstituted amino, substituted or unsubstituted aryl, substituted or unsubstituted heteroaryl, substituted or unsubstituted aralkyl, and the likes.

An electron withdrawing group means a functional group that tends to attract electrons through a triggering effect or a resonance effect, and includes, for example, halogens, cyano, substituted or unsubstituted amides, carbamates, sulfhydryl, nitro, carboxyl, carboxylic acid salts, quaternary ammonium, phosphoric acid, phosphates, ketones, aldehydes, esters, acyl chlorides, sulfonic acids, sulfonates, and the likes.

In one embodiment, at least one of $R_1$, $R_2$, $R_3$, and $R_4$ is a functional group selected from amino, hydroxyl, phosphoryl, aldehyde, carboxyl, and sulfhydryl, or a reactive group capable of covalently bonding to the functional group.

Examples of the reactive group include (a) a carboxyl group and a derivative thereof: N-hydroxysuccinimide ester, N-hydroxybenzotriazole ester, acyl halide, acyl imidazole, thioester, p-nitrophenyl ester, alkyl ester, alkenyl ester, alkynyl ester and aromatic ester; (b) hydroxyl which may be converted to an ester, an ether, or an aldehyde; (c) haloalkyl which can be covalently attached to another functional group by substituting a halogen with a nucleophilic functional group such as, for example, an amine, carboxylate anion, thiol anion, carbo anion or alkoxide ion; (d) for example, a nucleophile capable of carrying out a Daiels-Elder reaction with a maleimide group; (e) aldehydes or ketones capable of forming carbonyl derivatives such as imine, hydrazone, semicarbazone or oxime; (f) a sulfonyl halide which reacts with an amine to form a sulfoamide; (g) a thiol which is converted to a disulfide or is capable of reacting with an acyl halide; (h) amines or sulfhydryls which may be acylated, alkylated or oxidized; (i) alkenes capable of carrying out the reactions such as cyclization addition, acylation, Michael reaction and the like; (j) an epoxide capable of reacting with an amine or a hydroxyl compound; (k) phosphoramidite and other standard functional groups useful for the nucleic acid reactions, and the like. These reactive groups can be appropriately selected so as not to participate in or interfere with the reaction necessary to synthesize the reactive quencher.

In another embodiment, such reactive groups may be protected with a protecting group such that the reactive groups do not participate in any reaction in the presence of the protecting group. For example, when the reactive group is hydroxyl, the protecting group may be trialkylsilyl, 4,4-dimethoxytrityl or an analog thereof. Examples of preferred protecting groups can be found in the following references (Greene et al., PROTECTIVE GROUPS IN ORGANIC SYNTHESIS, John Wiley & Sons, New York, 1991).

The quencher according to the variety of the embodiments of the present invention can be labeled in combination with the target biomolecule (e.g., nucleic acid) through the reactive group described above.

The reactive groups described above are functional groups capable of reacting with a functional group such as an amino group, imino group, thiol group or hydroxyl group of the target biomolecule, and may form a covalent bond such as an amide bond, an imide bond, a urethane bond, an ester bond, a phosphite bond, a phosphate bond, or a guanidine bond between the quencher and the target biomolecule.

Since m and n are each independently an integer of 0 to 3, $R_5$ or $R_6$ may be 0 to 3.

X is O, S, $CR_7R_8$ or $SiR_7R_8$, Y is O or S, $R_7$ and $R_8$ may be selected each independently from substituted or unsubstituted $C_1$-$C_{10}$ alkyl, substituted or unsubstituted $C_2$-$C_{10}$ heteroalkyl including at least one heteroatom, substituted or unsubstituted aryl, and substituted or unsubstituted heteroaryl, or may be bonded to each other to form a ring.

$R_1$ and $R_2$ may be also bonded to each other to form a substituted or unsubstituted ring, or $R_1$ and/or $R_2$ may be bonded with adjacent $R_5$ to form a substituted or unsubstituted ring.

Further, $R_3$ and $R_4$ may be bonded to each other to form a substituted or unsubstituted ring, or $R_3$ and/or $R_4$ may be bonded with adjacent $R_6$ to form a substituted or unsubstituted ring.

When the functional groups adjacent to each other combine to form a substituted ring, any carbon in the ring may be a functional group selected from deuterium, substituted or unsubstituted $C_1$-$C_{40}$ alkyl, substituted or unsubstituted $C_1$-$C_{40}$ heteroalkyl including at least one heteroatom, substituted or unsubstituted $C_2$-$C_{40}$ alkenyl, substituted or unsubstituted $C_2$-$C_{40}$ alkynyl, substituted or unsubstituted $C_1$-$C_{40}$ alkoxy, substituted or unsubstituted aryloxy, substituted or unsubstituted $C_1$-$C_{40}$ haloalkyl, halogen, cyano, hydroxy, substituted or unsubstituted amino, substituted or unsubstituted amide, carbamate, sulfhydryl, nitro, carboxyl, carboxylate, substituted or unsubstituted aryl, substituted or unsubstituted heteroaryl, substituted or unsubstituted aralkyl, quaternary ammonium, phosphoric acid, phosphate, a ketone, an aldehyde, an ester, an acyl chloride, a sulfonic acid and a sulfonate, substituted or unsubstituted $C_1$-$C_{40}$ alkylthio, substituted or unsubstituted arylthio, substituted or unsubstituted $C_3$-$C_{20}$ cycloalkyl, substituted or unsubstituted $C_1$-$C_{20}$ heterocycloalkyl including at least one heteroatom, substituted or unsubstituted $C_3$-$C_{20}$ cycloalkenyl, substituted or unsubstituted $C_2$-$C_{20}$ heterocycloalkenyl containing at least one heteroatom, substituted or unsubstituted silyl, substituted or unsubstituted germanium, ether, nitrile, polyalkylene oxide, carboxyl, carboxyl derivative, hydroxyl, a haloalkyl, a nucleophile, an aldehyde, a ketone, a sulfonyl halide, a thiol, an amine, a sulfhydryl, an alkene, an epoxide, and a phosphoramidite; or may be substituted with at least one selected from a reactive group capable of covalently bonding to the above functional group.

When $R_1$, $R_2$, $R_3$, $R_4$, $R_5$, $R_6$, $R_7$, $R_8$, and R are substituted, any carbon in the functional group may be a functional group selected from deuterium, substituted or unsubstituted $C_1$-$C_{40}$ alkyl, substituted or unsubstituted $C_1$-$C_{40}$ heteroalkyl including at least one heteroatom, substituted or unsubstituted $C_2$-$C_{40}$ alkenyl, substituted or unsubstituted $C_2$-$C_{40}$ alkynyl, substituted or unsubstituted $C_1$-$C_{40}$ alkoxy, substituted or unsubstituted aryloxy, substituted or unsubstituted $C_1$-$C_{40}$ haloalkyl, halogen, cyano, hydroxy, substituted or unsubstituted amino, substituted or unsubstituted amide, carbamate, sulfhydryl, nitro, carboxyl, carboxylate, substituted or unsubstituted aryl, substituted or unsubstituted heteroaryl, substituted or unsubstituted aralkyl, quaternary ammonium, phosphoric acid, phosphate, a ketone, an aldehyde, an ester, an acyl chloride, a sulfonic acid and a sulfonate, substituted or unsubstituted $C_1$-$C_{40}$ alkylthio, substituted or unsubstituted arylthio, substituted or unsubstituted $C_3$-$C_{20}$ cycloalkyl, substituted or unsubstituted $C_1$-$C_{20}$ heterocycloalkyl including at least one heteroatom, substituted or unsubstituted $C_3$-$C_{20}$ cycloalkenyl, substituted or unsubstituted $C_2$-$C_{20}$ heterocycloalkenyl containing at least one heteroatom, substituted or unsubstituted silyl, substituted or unsubstituted germanium, ether, nitrile, polyalkylene oxide, carboxyl, carboxyl derivative, hydroxyl, a haloalkyl, a nucleophile, an aldehyde, a ketone, a sulfonyl halide, a thiol, an amine, a sulfhydryl, an alkene, an epoxide, and a phosphoramidite; or may be substituted with at least one selected from a reactive group capable of covalently bonding to the above functional group.

In the present specification, when Ra is alkenyl or alkynyl, the sp2-hybrid carbon of alkenyl or the sp-hybrid carbon of alkynyl may be in the form bonded either directly or indirectly by the sp3-hybrid carbon of alkyl which is bonded to the sp2-hybrid carbon of alkenyl or the sp-hybrid carbon of alkynyl.

The $C_a$-$C_b$ functional group herein refers to a functional group having a to b carbon atoms. For example, $C_a$-$C_b$ alkyl means a saturated aliphatic group including straight chain alkyl and branched chain alkyl having a to b carbon atoms. Straight chain or branched chain alkyl may have 40 or less of carbons in its backbone (e.g., a straight chain of $C_1$-$C_{10}$, branched chain of a $C_3$-$C_{10}$).

Specifically, the alkyl is selected from the group consisting of methyl, ethyl, n-propyl, i-propyl, n-butyl, s-butyl, i-butyl, t-butyl, pent-1-yl, pent-2-y, pent-3-yl, 3-methylbut-1-yl, 3-methylbut-2-yl, 2-methylbut-2-yl, 2,2,2-trimethylet-1-yl, n-hexyl, n-heptyl and n-octyl.

Further, alkoxy herein refers to both of —O— (alkyl) group and —O— (unsubstituted cycloalkyl) group, and is a straight chain or branched chain hydrocarbon having at least one of ether group and 1 to 10 carbon atoms.

Specifically, the alkoxy includes methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, cyclohexyloxy, and the like, but are not limited to them.

In addition, halogen herein refers to fluoro (—F), chloro (—Cl), bromo (—Br) or iodo (—I), and haloalkyl means alkyl substituted with halogen as described above. For example, halomethyl means methyl (—$CH_2X$, —$CHX_2$ or —$CX_3$) in which at least one of the hydrogens in methyl is replaced by halogen.

Aralkyl herein is a general term for —$(CH_2)_n$Ar, wherein aryl is a functional group of the form substituted in the carbon of the alkyl. Examples of aralkyl include benzyl (—$CH_2C_6H_5$) or phenethyl (—$CH_2CH_2C_6H_5$).

Unless otherwise defined herein, aryl means an unsaturated aromatic ring comprising a single ring or multiple rings (preferably one to four rings) joined together or covalently bonded to each other. Non-limiting examples of aryl include phenyl, biphenyl, o-terphenyl, m-terphenyl, p-terphenyl, 1-naphthyl, 2-naphthyl, 1-anthryl, 2-Anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl, 4-pyrenyl, and the like.

Heteroaryl herein refers to a functional group in which at least one of the carbon atom in the aryl as defined above is substituted with a non-carbon atom such as nitrogen, oxygen or sulfur. Non-limiting examples of heteroaryl include furyl, tetrahydrofuryl, phrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, Imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, Indolizinyl, indazolyl, quinolizinyl, quinolinyl, isoquinolinyl, cinnolinyl, phthalazinyl, quinazolinyl, quinoxalinyl, pteridinyl, quinuclidinyl, carbazoyl, acridinyl, phenazinyl, phenothizinyl, phenoxazinyl, purinyl, benzimidazolyl, benzothiazolyl, and the like; and analogues to which they are conjugated.

Cycloalkyl or heterocycloalkyl containing a heteroatom herein may be understood to be a cyclic structure of alkyl or heteroalkyl, respectively, unless otherwise defined.

Non-limiting examples of hydrocarbon rings include cyclopentyl, cyclohexyl, 1-cyclohexenyl, 3-cyclohexenyl, cycloheptyl, and the like. Non-limiting examples of hydrocarbon rings containing heteroatoms include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothiene-3-yl, 1-piperazinyl, 2-piperazinyl, and the like.

In addition, a hydrocarbon ring or a hydrocarbon ring containing a hetero atom may have a form in which a hydrocarbon ring, a hydrocarbon ring containing a hetero atom, an aryl or a heteroaryl is bonded or linked by a covalent bond.

The polyalkylene oxide herein is as a functional group of an aqueous polymer and include polyethylene glycol (PEG), polypropylene glycol (PPG), polyethylene glycol-polypropylene glycol (PEG-PPG) copolymer and N-substituted methacrylamide-containing polymer and copolymer.

The polyalkylene oxide may be additionally substituted as necessary to the extent that the properties of the polymer are maintained. For example, the substitution may be a chemical bond to increase or decrease the chemical or biological stability of the polymer. As a specific example, any carbon or terminal carbon in the polyalkylene oxide may be substituted with hydroxy, alkyl ether (methyl ether, ethyl ether, propyl ether, etc.), carboxylmethyl ether, carboxyethyl ether, benzyl ether, dibenzylmethylene ether, or dimethylamine. In one embodiment, the polyalkylene oxide may be a polyalkylene oxide (mPEG) terminated with methyl ether, wherein mPEG is represented by the formula —$(CH_2CH_2O)_nCH_3$, and the size of mPEG may vary depending on the size of n which corresponds to the number of ethylene glycol repeating units.

Further, the quencher represented by the formulas (1), (2), (5) and (6) may have a structure additionally comprising a counter ion. The counter ion can be appropriately selected in consideration of the solubility and stability of the quencher as an organic or inorganic anion.

Examples of the counter ions of the quencher according to one embodiment of the present invention include Inorganic acid anions such as phosphoric acid hexafluoride ion, halogen ion, phosphoric acid ion, perchloric acid ion, periodic acid ion, antimony hexafluoride ion, tartaric acid hexafluoride ion, fluoroboric acid ion, and tetrafluoride ion; and organic acid ions such as a thiocyanate ion, a benzenesulfonic acid ion, a naphthalenesulfonic acid ion, p-toluenesulfonic acid ion, an alkylsulfonic acid ion, a benzenecarboxylic acid ion, an alkylcarboxylic acid ion, a trihaloalkylcarboxylic acid ion, alkyl sulfonic acid ion, trihaloalkylsulfonic acid ion, and a nicotinic acid ion. In addition, metal compound ions such as bisphenylditol, thiobisphenol chelate and bisdiol-α-dikenton, metal ions such as sodium and potassium, and quaternary ammonium salts may also be selected as the counter ions.

Specific examples of the quencher represented by the formulas (1), (2), (5) and (6) are as follows:

[Compound 1]

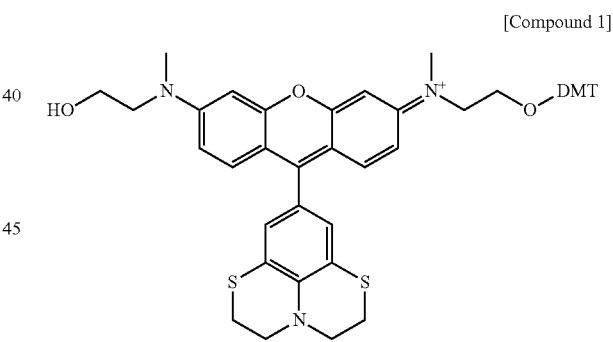

[Compound 2]

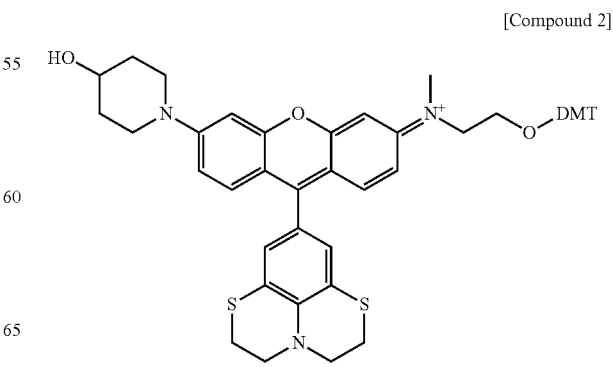

[Compound 3]
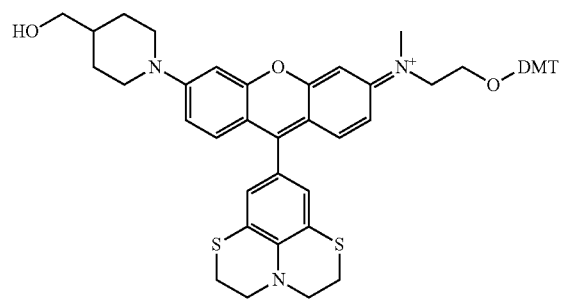
[Compound 4]
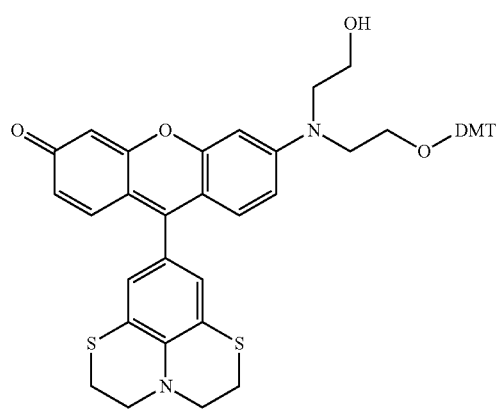
[Compound 5]
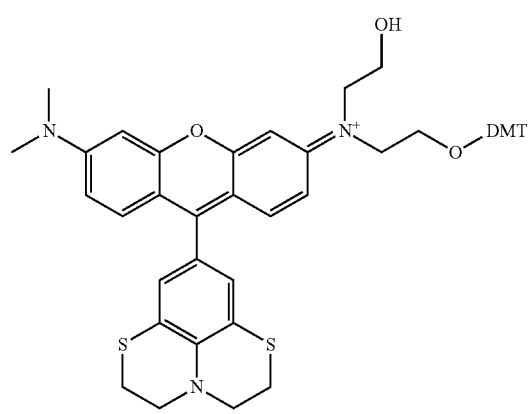
[Compound 6]
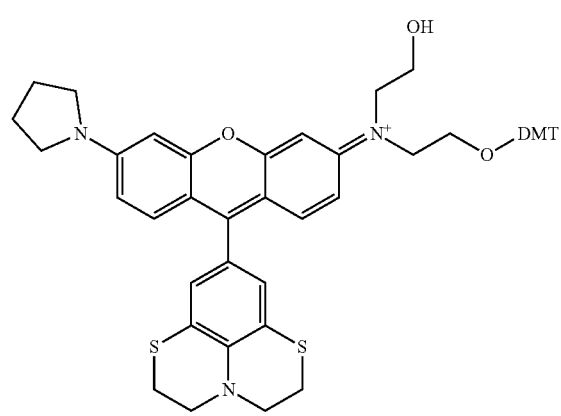
[Compound 7]
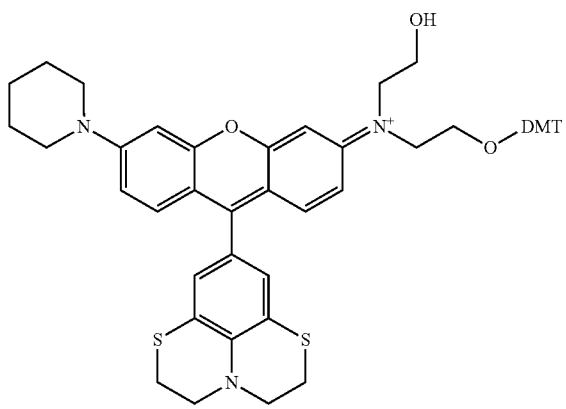
[Compound 8]
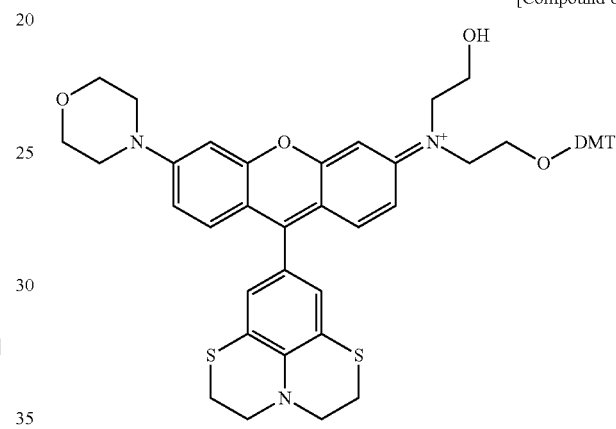
[Compound 9]
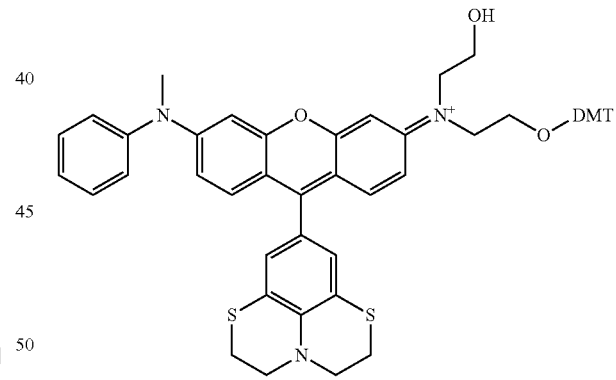
[Compound 10]
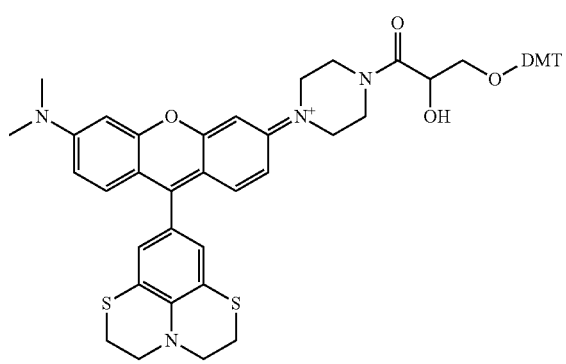

[Compound 11]
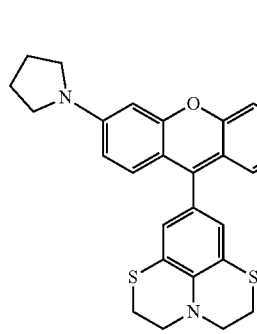
[Compound 15]
[Compound 12]
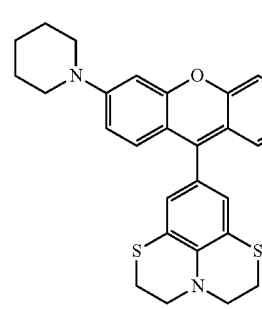
[Compound 16]
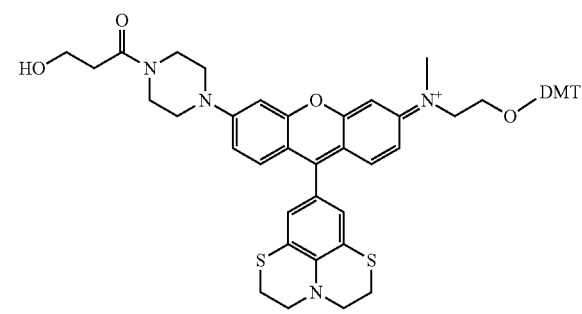
[Compound 17]
[Compound 13]
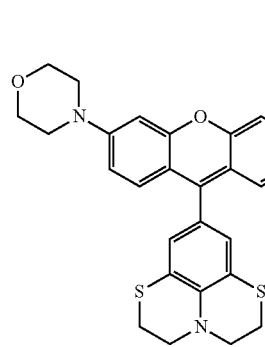
[Compound 18]
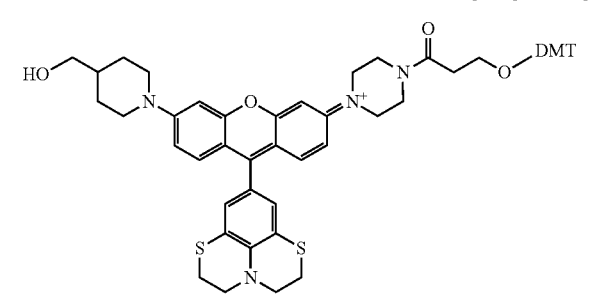
[Compound 14]
[Compound 19]
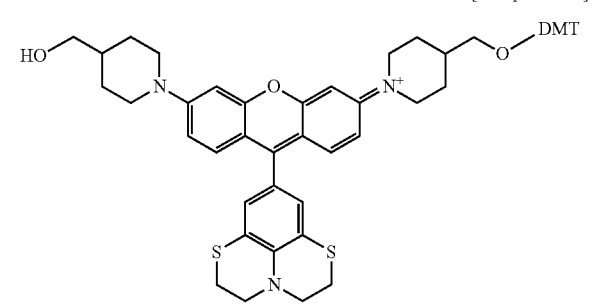
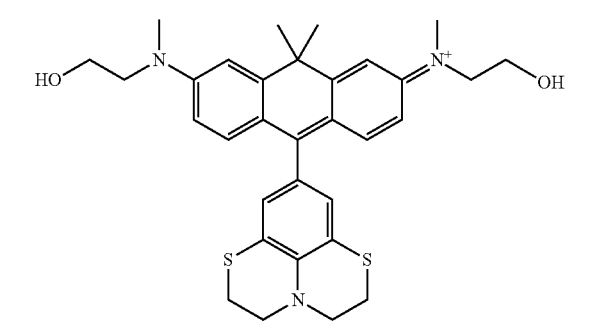

[Compound 20]

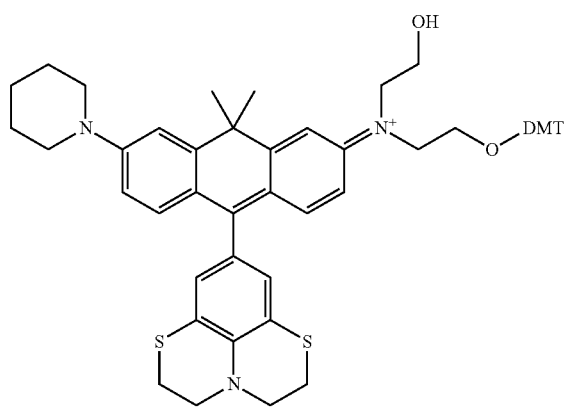

[Compound 21]

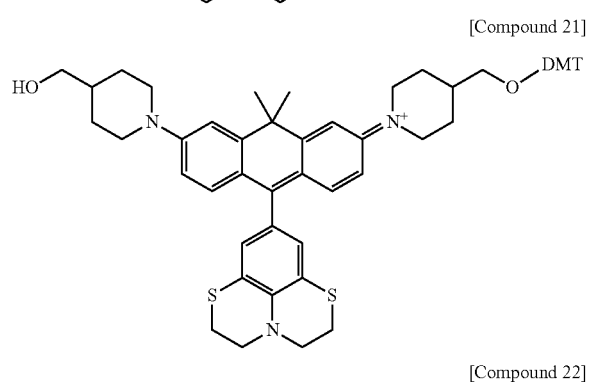

[Compound 22]

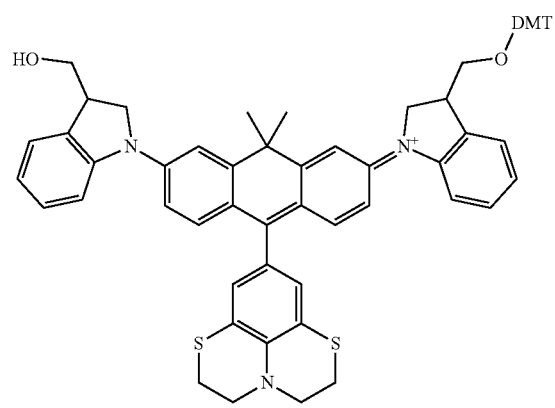

[Compound 23]

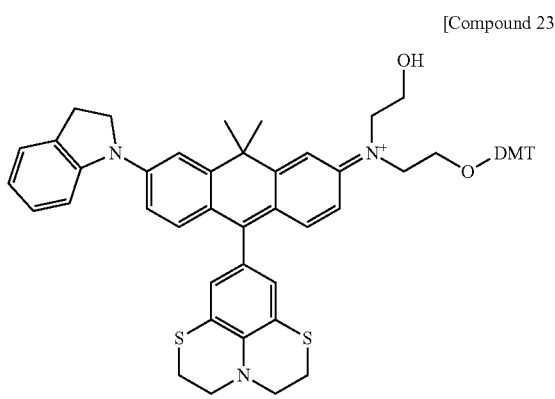

[Compound 24]

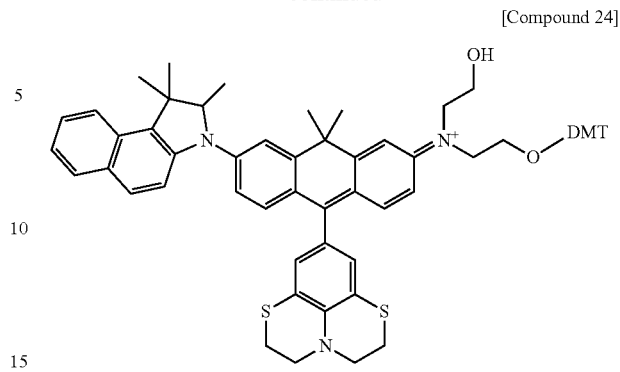

The biomolecules that are the target of the quencher represented by the formulas (1), (2), (5) and (6) disclosed herein may be at least one selected from antibodies, lipids, proteins, peptides, carbohydrates and nucleic acids (including nucleotides).

Specific examples of lipids include fatty acids, phospholipids, lipopolysaccharides and the like, and specific examples of carbohydrates include monosaccharides, disaccharides, and polysaccharides (e.g., dextran).

In this case, the biomolecules may be any functional groups of the quencher represented by the general formula (1), (2), (5) and (6) or the functional groups for reacting with a reactive group bonded to the quencher represented by the general formulas (1), (2), (5) and (6), and may include at least one selected from amino, sulphydryl, carbonyl, hydroxyl, carboxyl, phosphate and thiophosphate or may have a derivative thereof.

Further, the biomolecules may include at least one selected from amino, sulphydryl, carbonyl, hydroxyl, carboxyl, phosphate and thiophosphate, or may be an oxy or dioxy poly-nucleic acid having a derivative thereof.

Furthermore, in addition to the biomolecules, the quencher represented by the general formulas (1), (2), (5) and (6) may be used to label drugs, hormones (including receptor ligands), receptors, enzymes or enzyme substrates, cells, cell membranes, toxins, microorganisms, nano-bio materials (such as polystyrene microspheres), or the like, which include at least one selected from amino, sulphydryl, carbonyl, hydroxyl, carboxyl, phosphate and thiophosphate.

An Oligonucleotide, a Composition for Detecting a Nucleic Acid, a Support for Detecting the Nucleic Acid, which Comprise a Novel Quencher According to another aspect of the present invention, there is provided an oligonucleotide comprising at least one selected from the quenchers represented by the general formulas (1), (2), (5) and (6).

The oligonucleotide refers to a polymer of one to several hundred nucleotides and includes DNA, RNA, or PNA in all. In addition, oligonucleotide means to encompass analogues thereof, for example, those in which the nucleotide has been chemically modified or those in which the sugar has been conjugated, such that they can be easily modified by a person skilled in the art, and all of those of the single- or double-bond.

It is preferred that the oligonucleotide comprises a probe. More preferably, such a probe is that capable of complementarily binding with a target nucleic acid, but is not limited thereto. Herein, the probe may be selected from a nucleic acid, a peptide, a saccharide, an oligonucleotide, a protein, an antibody, or a combination thereof, but is not limited thereto.

In one embodiment, the oligonucleotide may comprise a fluorophore. For example, the fluorophore may be labeled at the 5' end of the oligonucleotide, and at least one selected from the quenchers represented by the general formulas (1), (2), (5) and (6) may be labeled at the 3' end of the oligonucleotide. The probe capable of complementarily binding to the target nucleic acid may be located between the 5' end and the 3' end.

The fluorophore may consult the type of fluorophore published in the following reference (Cardullo et al., Proc. Natl. Acad. Sci. USA 85: 8790-8794 (1988); Dexter, D. L., J. of Chemical Physics 21: 836-850 (1953); Hochstrasser et al., Biophysical Chemistry 45: 133-141 (1992); Selvin, P., Methods in Enzymology 246: 300-334 (1995); Steinberg, I. Ann. Rev. Biochem., 40: 83-114 (1971); Stryer, L. Ann. Rev. Biochem., 47: 819-846 (1978); Wang et al., Tetrahedron Letters 31: 6493-6496 (1990); Wang et al., Anal. Chem. 67: 1197-1203 (1995)).

Further, non-limiting examples of fluorescent moieties that can be used herein include 4-acetamido-4'-isothiocyanatostilbene-2,2'disulfonic acid, acridine and derivatives thereof, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin(7-amino-4-methylcoumarin (AMC, Coumarin 120), 7-amino-4-trifluoromethylcouluarin (Coumarin 151) and derivative thereof, cyan dye, cyanocyne, 4',6-diaminidino-2-phenylindole (DAPI), 5',5''-dibromopyrogallol-sulfonaphthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin and derivative thereof (eosin isocyanate), erythrosine and derivative thereof (erythrosine B, erythrosine isocyanate), itadium, flocaine and derivative thereof (5-carboxyflocaine (FAM)), 5-(4,6-dichlorotriazin-2-yl)aminofluorescein (DTAF), 2',7'-dimethoxy-4'5'-dichloro-6-carboxyfluorescein (JOE), QFITC (XRITC), fluorescamine, IR144, IR1446, Malachite Green isothiocyanate, 4-methylumbelliferone, ortho cresolphthalein, nitrotyrosine, pararosaniline, phenol red, B-phycoerythrin, o-Phthaldialdehyde, pyrene and derivative thereof (pyrene butyrate, succinimidyl 1-pyrene butyrate), quantum dots, Reactive Red 4 (Cibacron™ Brilliant Red 3B-A), rhodamine and derivative thereof (6-carboxy-X-rhodamine, 6-carboxydodamine, rhodamine B, rhodamine 123, rhodamine X isocyanate, sulforhodamine B, sulforhodamine 101, tetramethyl rhodamine, tetramethyl rhodamine isocyanate), riboflavin, rosolic acid, pyrene, carbopyronine, oxazine, xanthine, thioxanthine, terbium chelate derivatives, and the like.

In addition, the oligonucleotide according to the present invention may further include a minor groove binder (MGB) to improve bonding strength with a nucleic acid.

Such oligonucleotide can be utilized in a wide variety of chemical and biological fields. In particular, it may be useful for real-time polymerase chain reaction (PCR) or micro assay, but is not limited thereto.

According to another aspect of the present invention, there is provided a composition for detecting a nucleic acid, which comprises an oligonucleotide.

The composition for detecting the nucleic acid according to an embodiment of the present invention may further comprise an enzyme for reacting with the target biomolecule, a solvent (such as a buffer solution), other reagents, and the like, together with the quencher represented by the general formulas (1), (2), (5) and (6) and the oligonucleotide simultaneously containing a minor groove binder (MGB) and a fluorophore.

Herein, the solvent may include a buffer solution selected from the group consisting of phosphate buffer solution, carbonate buffer solution and a tris buffer solution, an organic solvent selected from dimethylsulfoxide, dimethylformamide, dichloromethane, methanol, ethanol and acetonitrile, and a water. It is possible to control the solubility by introducing the variety of the functional groups into the quencher depending on the kind of the solvents.

According to still another aspect of the present invention, there is provided a support for detecting a nucleic acid which comprises a quencher represented by the general formulas (1), (2), (5) and (6), a support, and a linker connecting the quencher and the support.

Thus, the biomolecules in the sample can be immobilized on the support matrix through interaction with the quencher immobilized on the support.

The support matrix may be prepared with at least one selected from the group consisting of glass, cellulose, nylon, acrylamide gel, dextran, polystyrene, alginate, collagen, peptide, fibrin, hyaluronic acid, agarose, polyhydroxyethyl methacrylate, polyvinyl alcohol, polyethylene glycol, polyethylene oxide, polyethylene glycol diacrylate, gelatin, matrigel, polylactic acid, carboxymethylcellulose, dextran, chitosan, latex and sepharose, and may have a type of beads or membranes.

The linker connects the quencher and the support, and any material capable of connecting the quencher and the support may be used as the linker which is intended herein.

For example, the linker may be selected from substituted or unsubstituted $C_1$-$C_{30}$ alkyl, substituted or unsubstituted $C_2$-$C_{30}$ heteroalkyl having at least one heteroatom, substituted or unsubstituted $C_6$-$C_{30}$ aryl, and substituted or unsubstituted $C_3$-$C_{30}$ heteroaryl, and more specifically, may be a chain to which 1 to 6 ethylene glycols are linked.

Such a linker connects the quencher and the support only and does not affect other reaction or fluorescence-extinction of the quencher or the fluorophore.

A Method for Detecting a Nucleic Acid

According to one embodiment of the present invention, a method for reacting and labeling a probe labeled with a quencher to a target nucleic acid can be implemented. In addition, the present invention can implement a method for labeling a biomolecule using a target-specific interaction by introducing an appropriate reactive group into a quencher depending on the kind of the target biomolecule. Further, the present invention may implement a method for identifying a biomolecule labeled with a quencher through the electrophoresis.

A Method for DNA Microarray

In a method for DNA microarray, a probe nucleic acid of a single chain having a base sequence complementary to a target nucleic acid is prepared by reacting the target nucleic acid to be labeled with a dye, and the target nucleic acid modified to the single chain and the probe nucleic acid are hybridized on a substrate to measure fluorescence of the target nucleic acid.

The probe nucleic acid immobilized on a substrate in this labeling method can be prepared by amplifying a library of cDNA such as cDNA, a library of a genome, or all genomes as a template with a PCR method, when the expression of a gene is examined.

In the case of examining mutation of a gene, it is possible to use a synthesized oligonucleotide corresponding to the mutation based on the standard sequence as already known.

The immobilization of the probe nucleic acid on the substrate can be appropriately selected depending on the kind of the nucleic acid or the type of the substrate. For example, it may be able to use a method of performing electrostatic bonding to the substrate surface-treated with a cation such as polylysine using charge of DNA.

The target nucleic acid modified to the single chain is immobilized on the substrate and hybridized with the oligonucleotide, whereby a fluorophore is labeled at the 5' end of the oligonucleotide, at least one selected from the quenchers represented by the general formulas (1), (2), (5) and (6) is labeled at the 3' end. A probe capable of complementarily binding to the target nucleic acid may be located between the 5' end and the 3' end of the oligonucleotide.

The hybridization is preferably performed at a temperature in the range of room a temperature to 70° C. for the period of 2 to 48 hours. By the hybridization, a target nucleic acid having a base sequence complementary to the probe nucleic acid selectively binds to the probe nucleic acid. Thereafter, the substrate is cleaned and dried at a room temperature.

In this case, the oligonucleotide is hybridized to the target nucleic acid by the probe, but the fluorophore at the 5' end exists in a state quenched by the quencher at the 3' end.

Then, the oligonucleotide hybridized to the target nucleic acid is elongated by the polymerase, which is separated and cleaved from the target nucleic acid by the exonuclease activity of the polymerase, and the fluorophore at the 5' end of the oligonucleotide and the quencher at the 3' end thereof is separated from each other, so that the fluorophore can emit fluorescence.

At this time, the amount of amplification of the target nucleic acid can be determined by measuring the fluorescence intensity to be generated.

Hereinafter, specific embodiments of the present invention will be described. It should be understood that the examples described below are to illustrate or explain the present invention only, but are not intended to be limiting the present invention.

Preparation Example 1. Synthesis of Compound 4

Synthesis of Intermediate 1

Starting material (10 g, 20.31 mmol), amine (32.5 g, 101.56 mmol) and dimethylsulfoxide (100 ml) were added to 250 ml of a one-necked reactor and stirred at 60° C. for 48 hours. After cooling, water (100 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and purified by the column. (1.8 g, 3.309 mmol, 11%)

Synthesis of Intermediate 2

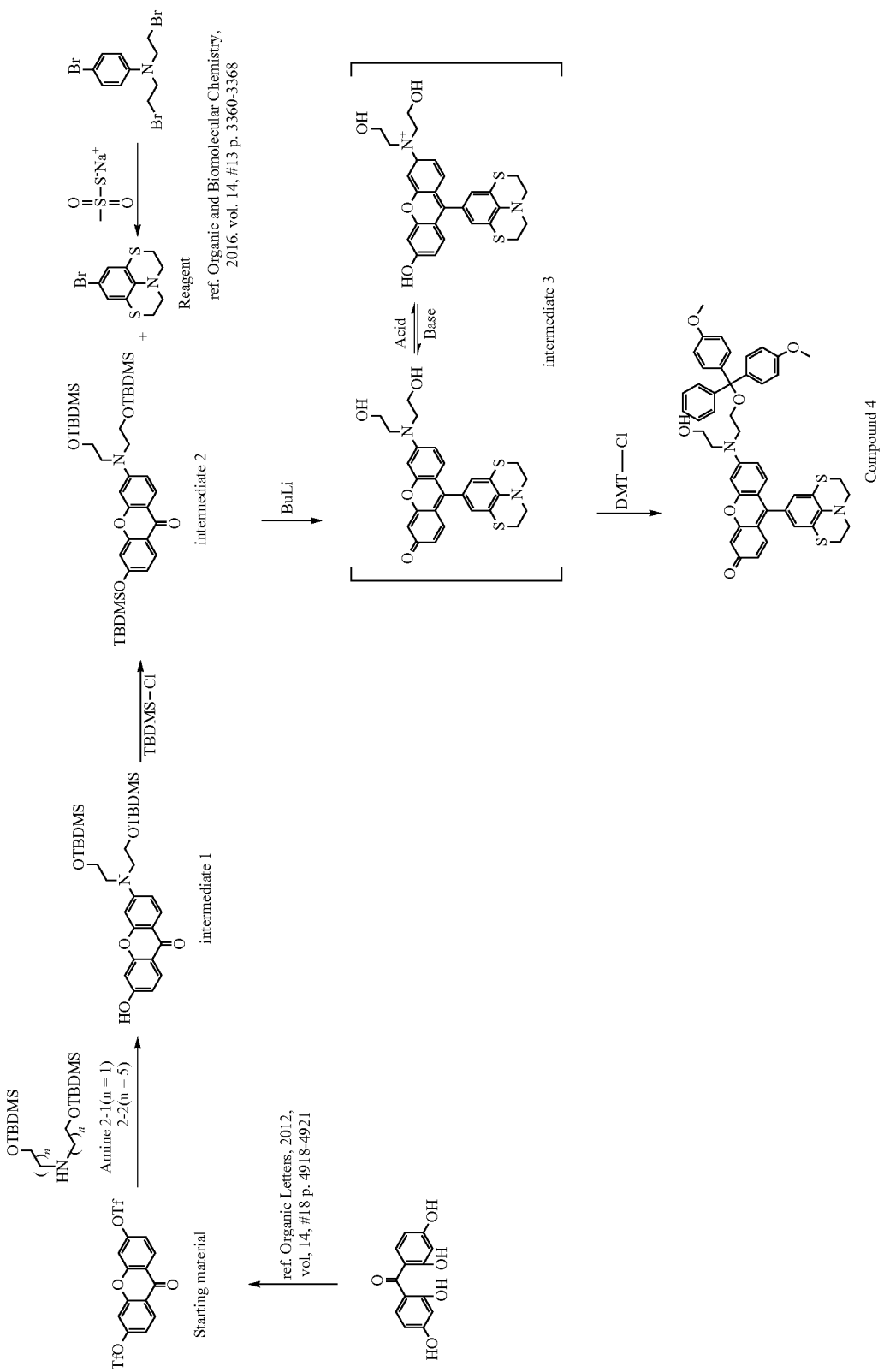

Intermediate 1 (1.8 g, 3.309 mmol), imidazole (0.68 g, 9.929 mmol), tert-butyl-di-methylchlorosilane (0.75 g, 4.964 mmol) and dimethylformamide (20 ml) was added to 100 ml of a one-necked reactor and the mixture was stirred at a room temperature for 1 hour. Ethyl acetate (80 ml) was added to the reactor and washed with brine (200 ml×2). Anhydrous magnesium sulfate was added to the organic layer, and after the mixture was stirred for 5 minutes, the solid was filtered. The filtrate was concentrated and purified by the column. (1.37 g, 2.081 mmol, 63%).

Synthesis of Intermediate 3

Reagent (1.2 g, 4.163 mmol) and tetrahydrofuran (15 ml) were added to 250 ml of a three-necked reactor, and the mixture was stirred under a nitrogen stream at −78° C. for 5 minutes.

1.6 M of n-butyllithium (2 ml, 3.121 mmol) was slowly added dropwise to the reactor, followed by stirring at −78° C. for 1 hour. Intermediate 2 (1.37 g, 2.081 mmol) was dissolved in tetrahydrofuran (15 ml), added dropwise to the reactor, and then stirred at a room temperature for 12 hours. 2 M of hydrochloric acid (10 ml) was added to the reactor and stirred strongly for 30 minutes. After concentration, the mixture was purified by the column. (0.76 g, 1.5 mmol, 72%).

Synthesis of Compound 4

Intermediate 3 (130 mg, 0.375 mmol), 4,4'-dimethoxytrityl chloride (130 mg, 0.375 mmol), 4-(dimethylamino)pyridine (45 mg, 0.375 mmol) and dimethylformamide (2 ml) was added to 250 ml of a one-necked reactor and the mixture was stirred at a room temperature for 12 hours. After concentration, the mixture was purified by the column. (20 mg, 0.0247 mmol, 7%) 1H-NMR (300 MHz, CDCl3) δ 7.36-7.33 (m, 2H), 7.26-7.11 (m, 10H), 6.72 (d, 4H, J=8.7 Hz), 4.65-6.62 (m, 3H), 6.48-6.40 (m, 2H), 3.99-3.97 (m, 2H), 3.90-3.49 (m, 14H), 3.22 (m, 3H), 3.09 (m, 3H)

Preparation Example 2. Synthesis of Compound 7

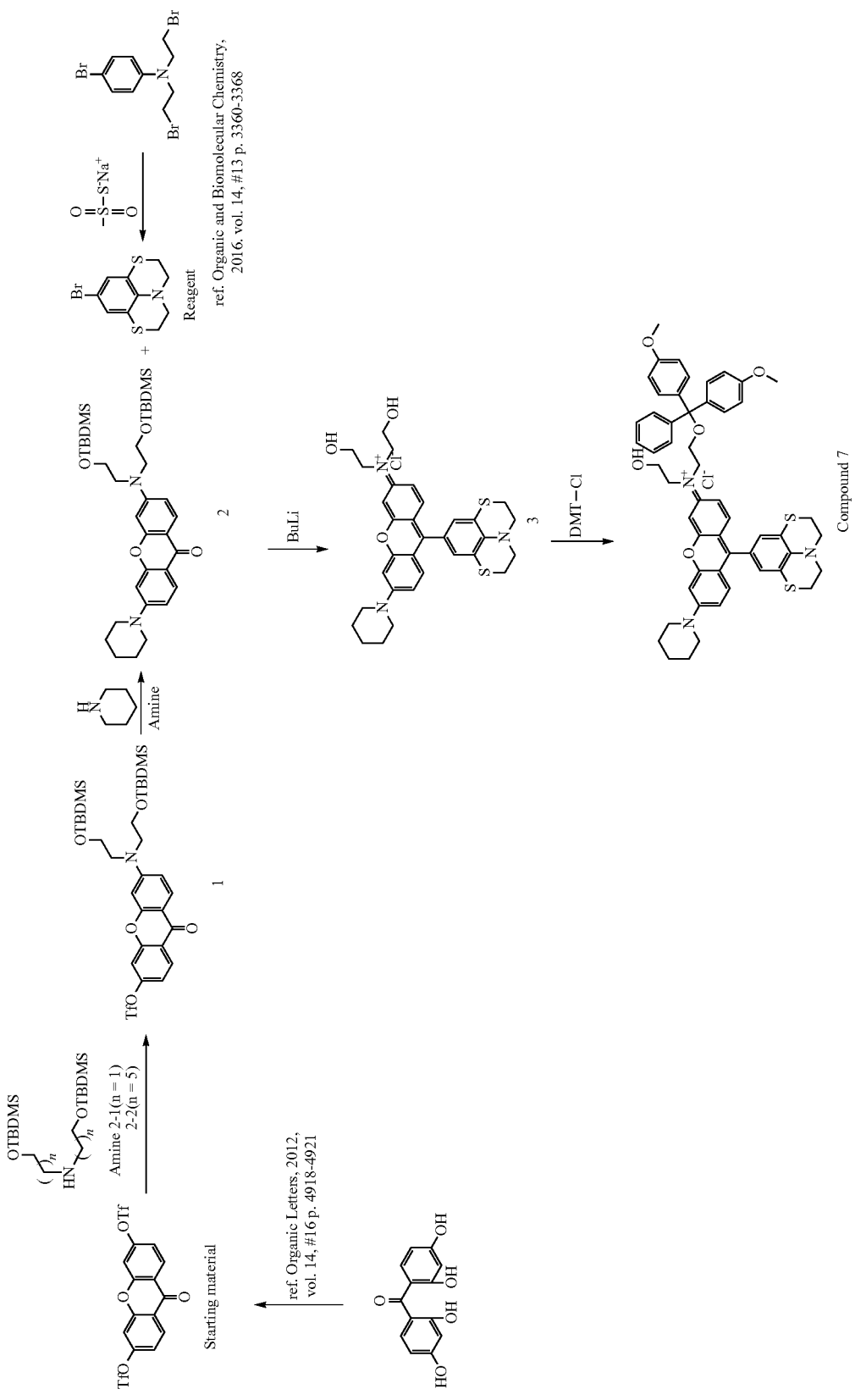

Synthesis of Intermediate 1

Starting material (10 g, 20.31 mmol), amine (32.5 g, 101.56 mmol) and dimethylsulfoxide (100 ml) were added to 250 ml of a one-necked reactor and stirred at 60° C. for 48 hours. After cooling, water (100 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and purified by the column. (10.11 g, 14.9 mmol, 73%)

Synthesis of Intermediate 2

Intermediate 1 (8.2 g, 14.9 mmol), amine (10 ml, 149 mmol) and dimethyl sulfoxide (80 ml) was added to 250 ml of a one-necked reactor and the mixture was stirred at 90° C. for 1 hour.

After cooling, water (100 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and purified by the column. (5.17 g, 8.46 mmol, 57%)

Synthesis of Intermediate 3

Reagent (8.78 g, 30.46 mmol) and tetrahydrofuran (90 ml) were added to 250 ml of a three-necked reactor, and the mixture was stirred under a nitrogen stream at −78° C. for 5 minutes.

1.6 M of n-butyllithium (15.8 ml, 25.38 mmol) was slowly added dropwise to the reactor, followed by stirring at −78° C. for 1 hour. Intermediate 2 (5.17 g, 8.46 mmol) was dissolved in tetrahydrofuran (20 ml), added dropwise to the reactor, and then stirred at a room temperature for 12 hours. 2 M of hydrochloric acid (20 ml) was added to the reactor and stirred strongly for 30 minutes. After concentration, the mixture was purified by the column. (4.5 g, 7.37 mmol, 87%)

Synthesis of Compound 7

Intermediate 3 (1.8 g, 2.949 mmol), 4,4'-dimethoxytrityl chloride (1 mg, 2.949 mmol), 4-(dimethylamino) pyridine (0.36 g, 2.949 mmol) and pyridine (20 ml) was added to 250 ml of a one-necked reactor and the mixture was stirred at a room temperature for 12 hours. After concentration, the mixture was purified by the column. (1.8 g, 1.972 mmol, 67%) 1H-NMR (300 MHz, CDCl3) δ 7.60 (m, 2H), 7.54-7.51 (m, 2H), 7.41-7.14 (m, 9H), 6.97-6.86 (m, 4H), 6.76 (d, 4H, 8.4 Hz), 4.96 (bs, 1H), 3.91-3.60 (m, 20H), 3.46 (m, 2H), 3.16-3.12 (m, 4H), 1.77 (m, 6H)

Preparation Example 3. Synthesis of Compound 12

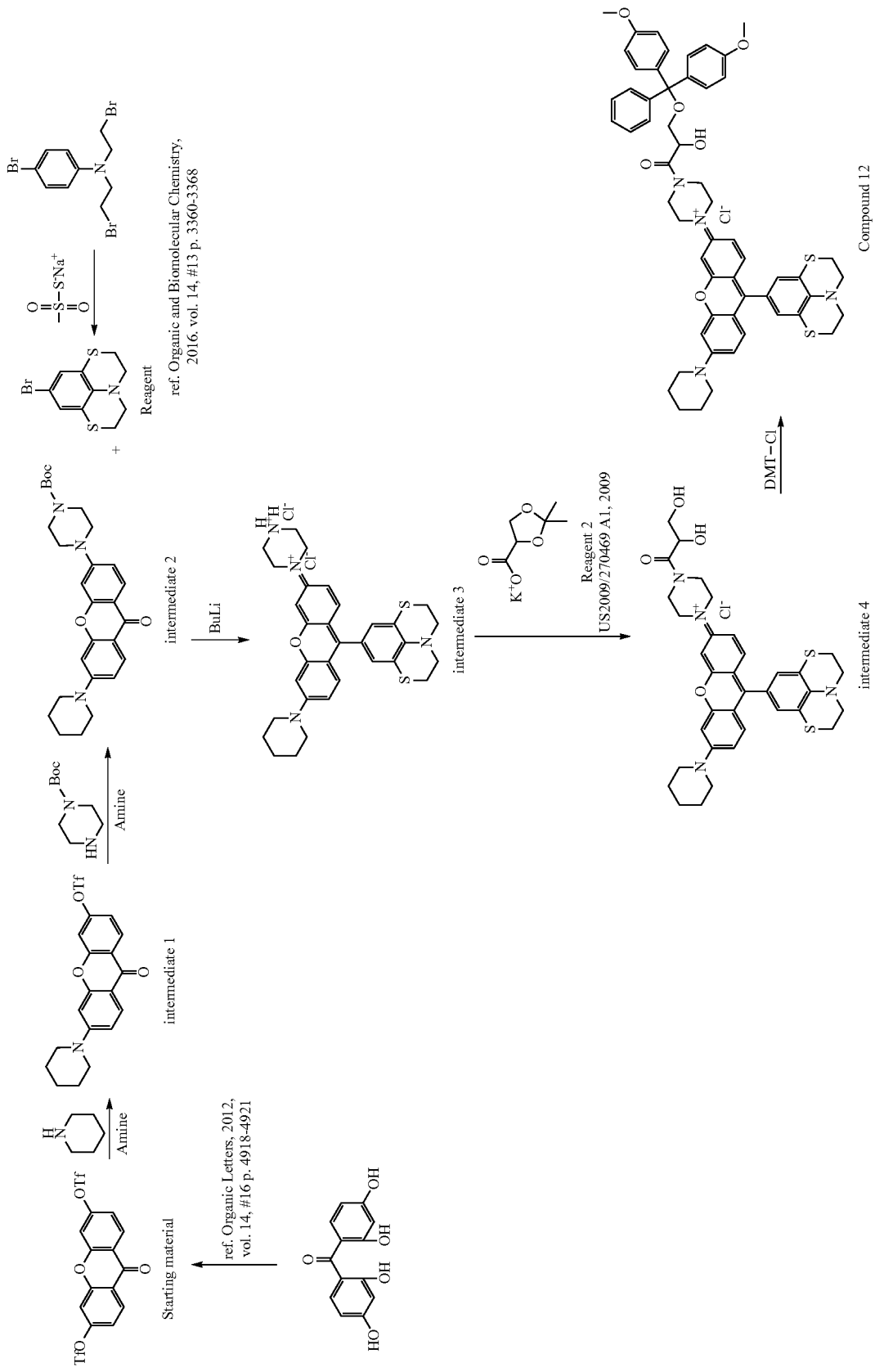

Synthesis of Intermediate 1

Starting material (10 g, 20.31 mmol), amine (10 ml, 101.56 mmol) and dimethylsulfoxide (100 ml) were added to 250 ml of a one-necked reactor and stirred at a room temperature for 2 hours. After cooling, water (100 ml) was added to the reactor, the mixture was stirred strongly, and then extracted with dichloromethane (100 ml×2). Anhydrous magnesium sulfate was added to the organic layer, and after the mixture was stirred for 5 minutes, the solid was filtered. The filtrate was concentrated and purified by the column. (5.82 g, 13.62 mmol, 67%)

Synthesis of Intermediate 2

Intermediate 1 (2.3 g, 5.381 mmol), amine (5 g, 26.9 mmol) and dimethyl sulfoxide (20 ml) was added to 250 ml of a one-necked reactor and the mixture was stirred at 90° C. for 6 hours.

After cooling, water (300 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and recrystallized. (2.08 g, 4.486 mmol, 83%)

Synthesis of Intermediate 3

Reagent (6.5 g, 22.52 mmol) and tetrahydrofuran (70 ml) were added to 250 ml of a three-necked reactor, and the mixture was stirred under a nitrogen stream at −78° C. for 5 minutes.

1.6 M of n-butyllithium (11.73 ml, 18.77 mmol) was slowly added dropwise to the reactor, followed by stirring at −78° C. for 1 hour. Intermediate 2 (2.9 g, 6.26 mmol) was dissolved in tetrahydrofuran (20 ml), added dropwise to the reactor, and then stirred at a room temperature for 12 hours. 2 M of hydrochloric acid (20 ml) was added to the reactor and stirred strongly for 30 minutes. A next reaction was carried out without purifying after concentration.

Synthesis of Intermediate 4

Intermediate (2.82 g), Reagent 2 (0.82 g, 4.46 mmol), O-(Benzotriazol-1yl)-N, N, N', N'-tetramethyluronium tetrafluoroborate (1.72 g, 5.35 mmol), triethylamine (1.9 ml, 13.38 mmol) and dimethylformamide (30 ml) were added to 250 ml of a one-necked reactor, and the mixture was stirred at a room temperature for 3 hours. The mixture was concentrated and purified. To the mixture was added dichloromethane (10 ml) and 4M hydrochloric acid (4 ml), and the mixture was stirred at a room temperature for 2 hours, followed by concentrated and purified by the column. (130 mg, 0.191 mmol)

Synthesis of Compound 12

Intermediate 4 (130 mg, 0.191 mmol), 4-(dimethylamino) pyridine (23 mg, 0.191 mmol) and pyridine (1 ml) was added to 50 ml of a one-necked reactor and the mixture was stirred at a room temperature for 72 hours. After concentration, the mixture was purified by the column. (65 mg, 0.0662 mmol, 35%) 1H-NMR (300 MHz, CDCl3) δ 7.64-7.59 (m, 2H), 7.41 (d, 2H, 8.4 Hz), 7.31-7.01 (m, 11H), 6.88 (s, 2H), 6.82-6.78 (m, 4H), 4.63-6.61 (m, 1H), 4.21-4.18 (m, 1H), 4.05-3.24 (m, 23H), 3.16-3.13 (m, 4H), 1.80-1.74 (m, 6H)

Preparation Example 4. Synthesis of Compound 18

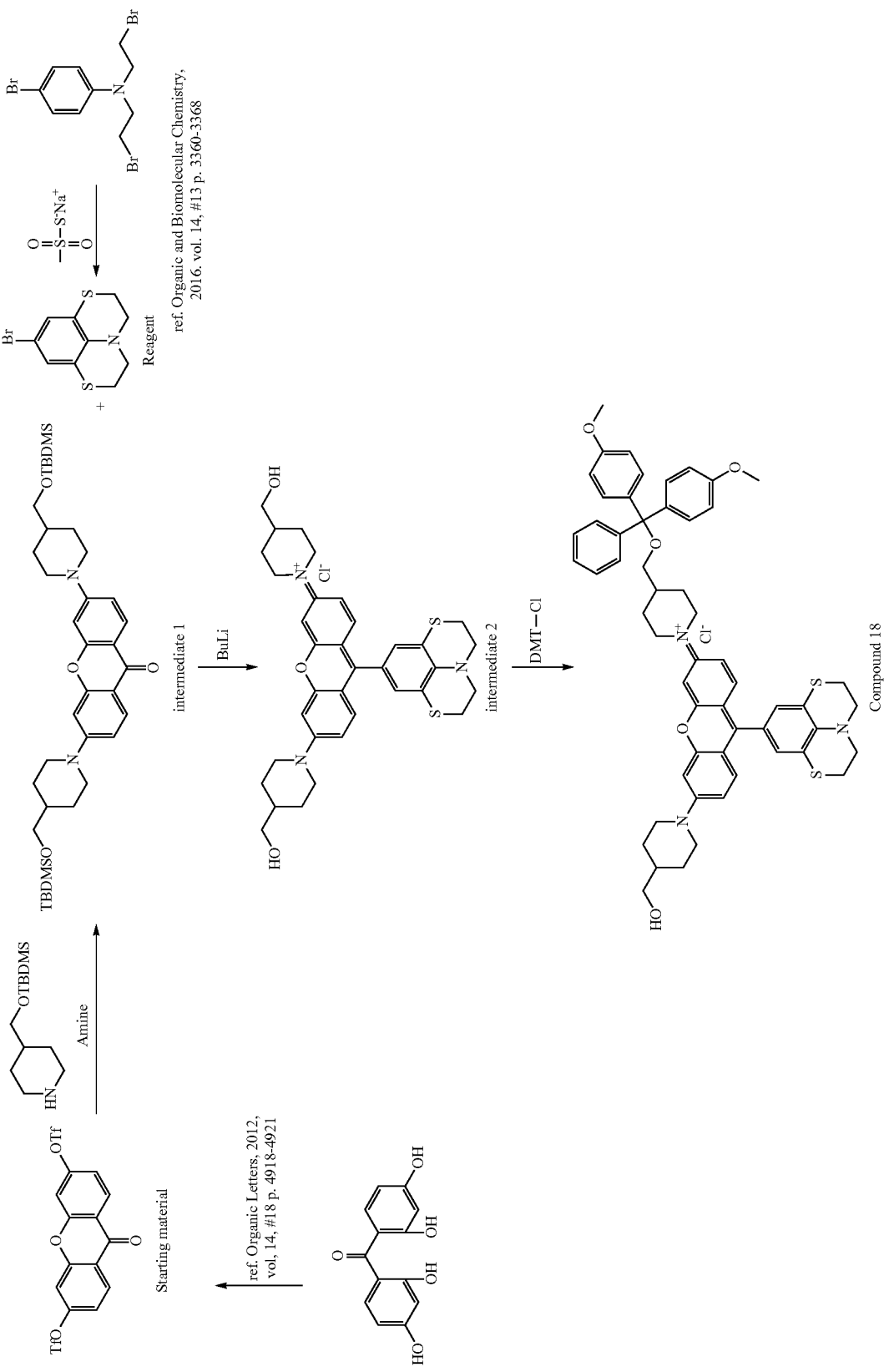

Synthesis of Intermediate 1

Starting material (2 g, 4.062 mmol), amine (9.32 ml, 40.62 mmol) and dimethylsulfoxide (20 ml) were added to 250 ml of a one-necked reactor and stirred at 60° C. for 12 hours. After cooling, water (100 ml) was added to the reactor, the mixture was stirred strongly, and then extracted with dichloromethane (100 ml×2). Anhydrous magnesium sulfate was added to the organic layer, and after the mixture was stirred for 5 minutes, the solid was filtered. The filtrate was concentrated and purified by the column. (0.8 g, 1.228 mmol, 30%)

Synthesis of Intermediate 2

Reagent (0.93 g, 3.225 mmol) and tetrahydrofuran (10 ml) were added to 100 ml of a three-necked reactor, and the mixture was stirred under a nitrogen stream at −78° C. for 5 minutes.

1.6 M of n-butyllithium (3 ml, 4.838 mmol) was slowly added dropwise to the reactor, followed by stirring at −78° C. for 1 hour. Intermediate 1 (0.7 g, 1.075 mmol) was dissolved in tetrahydrofuran (10 ml), added dropwise to the reactor, and then stirred at a room temperature for 12 hours. 2 M of hydrochloric acid (10 ml) was added to the reactor and stirred strongly for 30 minutes. After concentration, the mixture was purified by the column. (0.28 g, 0.430 mmol, 40%)

Synthesis of Compound 18

Intermediate 2 (280 mg, 0.430 mmol), 4, 4'-dimethoxytrityl chloride (145 mg, 0.430 mmol) and pyridine (5 ml) was added to 50 ml of a one-necked reactor and the mixture was stirred at a room temperature for 48 hours. After concentration, the mixture was purified by the column. 37 mg, 0.0388 mmol, 9%) 1H-NMR (300 MHz, CDCl3) δ 7.58-7.53 (m, 2H), 7.43-7.40 (m, 2H), 7.31-7.20 (m, 7H), 7.07-7.04 (m, 2H), 6.89-6.81 (m, 8H), 4.23-4.18 (m, 4), 3.78 (m, 10H), 3.57 (m, 2H), 3.34-3.22 (m, 4H), 3.16-3.13 (m, 4H), 3.00-2.98 (m, 2H), 2.05-2.02 (m, 6H), 1.47-1.34 (m, 4H)

Preparation Example 5. Synthesis of Compound 20

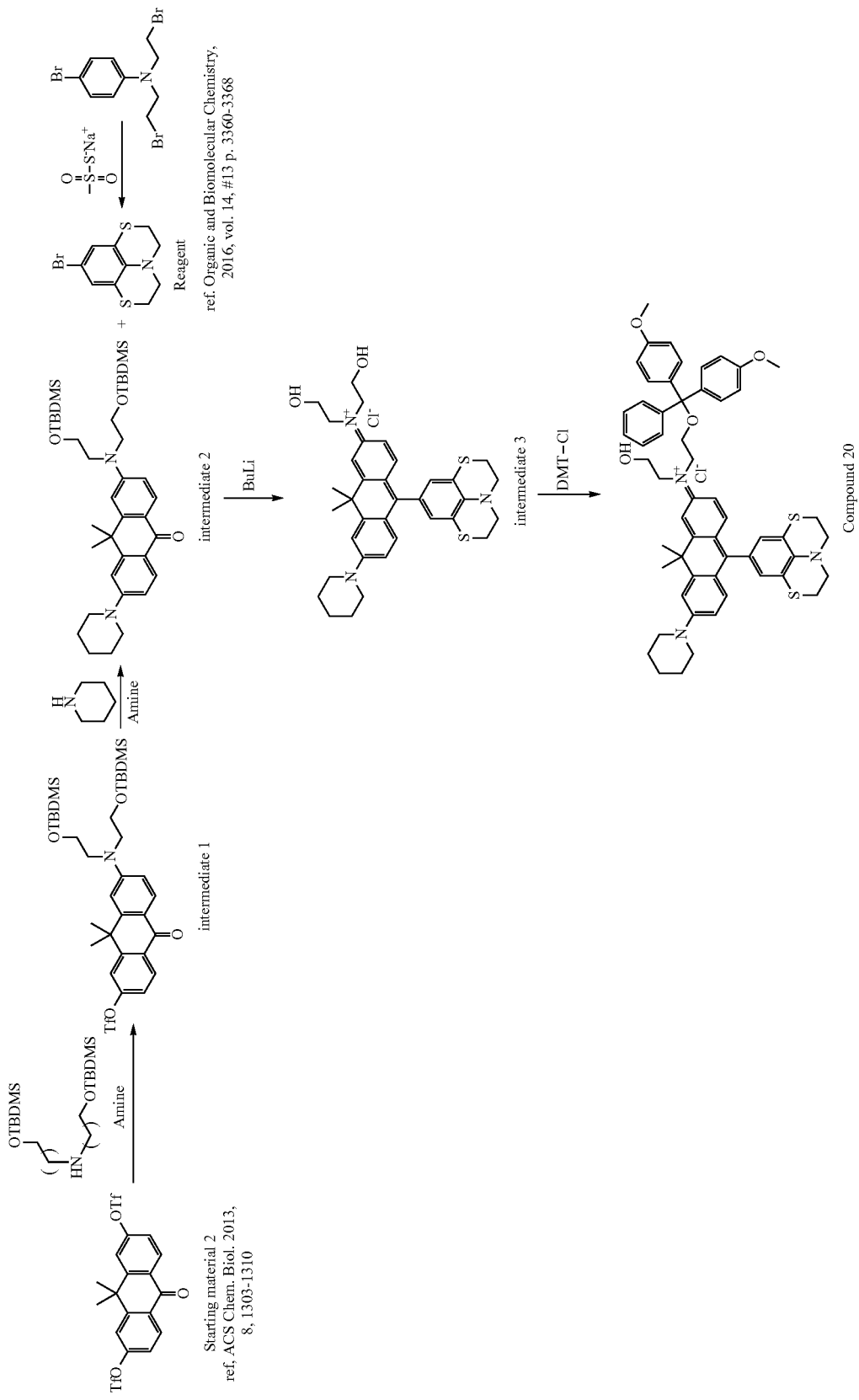

Synthesis of Intermediate 1

Starting material 2 (2 g, 3.858 mmol), amine (6.43 g, 19.29 mmol) and dimethylsulfoxide (20 ml) were added to 100 ml of a one-necked reactor and stirred at 60° C. for 48 hours. After cooling, water (100 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and purified by the column. (0.87 g, 1.239 mmol, 32%)

Synthesis of Intermediate 2

Intermediate 1 (0.87 g, 1.239 mmol), amine (1.2 ml, 12.39 mmol) and dimethyl sulfoxide (10 ml) was added to 50 ml of a one-necked reactor and the mixture was stirred at 90° C. for 1 hour.

After cooling, water (100 ml) was added to the reactor, the mixture was stirred strongly, and then extracted with ethyl acetate (100 ml×2). Anhydrous magnesium sulfate was added to the organic layer, and after the mixture was stirred for 5 minutes, the solid was filtered. The filtrate was concentrated and purified by the column. (500 mg, 0.785 mmol, 63%)

Synthesis of Intermediate 3

Reagent (0.68 g, 2.354 mmol) and tetrahydrofuran (5 ml) were added to 50 ml of a three-necked reactor, and the mixture was stirred under a nitrogen stream at −78° C. for 5 minutes.

1.4 M of sec-butyllithium (1.7 ml, 2.354 mmol) was slowly added dropwise to the reactor, followed by stirring at −78° C. for 1 hour. Intermediate 2 (500 mg, 0.785 mmol) was dissolved in tetrahydrofuran (5 ml), added dropwise to the reactor, and stirred at a room temperature for 12 hours. 2 M of hydrochloric acid (3 ml) was added to the reactor and stirred strongly for 30 minutes. After concentration, the mixture was purified by the column. (380 mg, 0.597 mmol, 76%)

Synthesis of Compound 20

Intermediate 3 (380 mg, 0.97 mmol), 4,4'-dimethoxytrityl chloride (200 mg, 0.597 mmol), 4-(dimethylamino) pyridine (73 mg, 0.597 mmol) and pyridine (5 ml) was added to 100 ml of a one-necked reactor and the mixture was stirred at a room temperature for 12 hours. After concentration, the mixture was purified by the column.

Preparation Example 6. Synthesis of Quencher-CPG

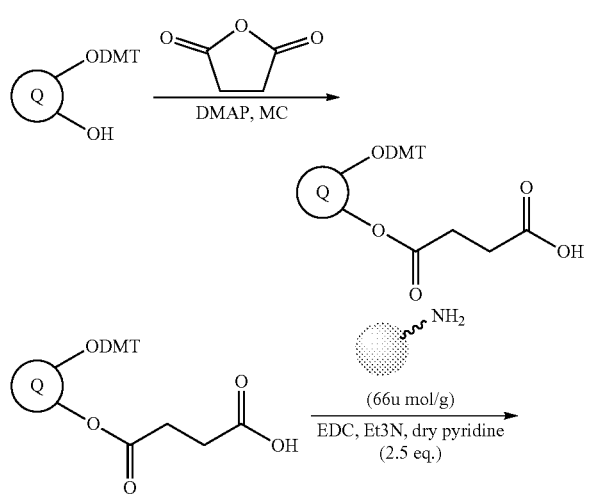

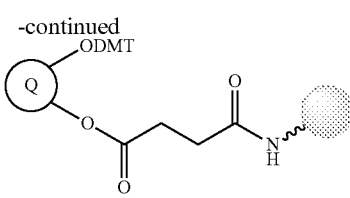

To 10 ml of a vial was added compound 7 (100 mg, 0.11 mmol), succinic anhydride (9.9 mg, 0.099 mmol), 4-dimethylaminopyridine (12.1 mg, 0.099 mmol) and dichloromethane (5 ml), and the reaction mixture was rolled at a room temperature for 1.5 hours. The reaction mixture was fully concentrated and treated with 1-ethyl-3-(3-dimethylaminopropyl)carbodiimide (52.7 mg, 0.275 mmol), triethylamine (28 ul), pyridine (5 ml) and CPG-NH2 (1 g), and was rolled at a room temperature for 2 hours. The powder was filtered and wash three times with acetonitrile, methanol, and dichloromethane, respectively. After drying, CapA/CapB=1 ml/1 ml was added to the powder, which was then rolled at a room temperature for 2 hours, washed with acetonitrile and dichloromethane three times and dried. (1 g, Molecular loading: 37 umol/g)

The following Table 1 shows the molecular loading for each of the compounds when the quencher-CPG was synthesized using Compound 4, Compound 12, and Compound 18 in the same manner as Preparation Example 6 described above.

TABLE 1

| Compound | Molecular loading (umol/g) |
|---|---|
| Compound 4 | 39.5 |
| Compound 7 | 37 |
| Compound 12 | 27 |
| Compound 18 | 60 |

Preparation Example 7. Synthesis of Oligonucleotide

An oligonucleotide was synthesized with Compound 7 using 10-Column Polygen DNA Synthesizer. The UV spectrum of the synthesized oligonucleotide is shown in FIG. 1.

Experimental Examples. Measurement of Quenching Properties of a Quencher

Experimental Example 1

λMax(nm) and Absorption coefficient(e) of Compound 4, Compound 7, Compound 12, Compound 18 and Compound 20 prepared according to Preparation Examples 1 to 5 were confirmed. The results are shown in FIG. 2 and Table 2.

TABLE 2

| Compound | $\lambda_{Max}$ (nm) | Absorption coefficient(e) |
|---|---|---|
| Compound 4 | 520 | 41,000 |
| Compound 7 | 558 | 69,000 |
| Compound 12 | 556 | 50,000 |
| Compound 18 | 560 | 14,000 |
| Compound 20 | 620 | 87,000 |
| Compound 24 | 660 | 48,000 |

Figure 2:
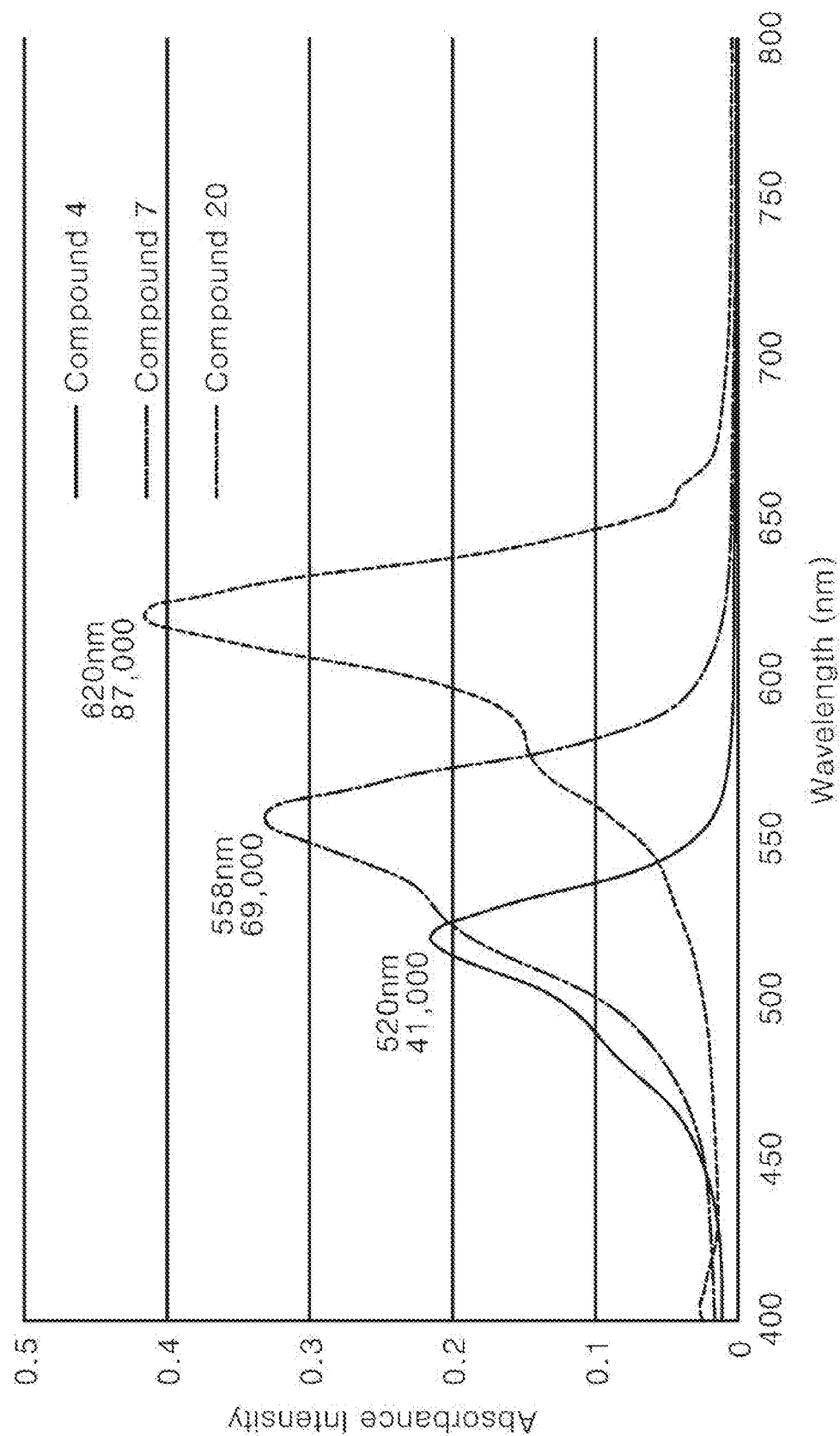
FIGS. 2 to 6 show the quenching characteristics of a double-labeled probe denoted by a quencher according to an embodiment of the present invention and a quencher according to a comparative example.

Referring to the results of FIG. 2 and Table 2, it can be seen that the quenchers according to various embodiments of the present invention exhibit the absorption characteristics at wavelengths of 450 nm or more. Accordingly, it is possible to design a double-labeled probe through combination with a variety of the fluorophores.

Experimental Example 2

After the double-labeled probe was designed as shown in Table 3 below, the quenching characteristics of each double-labeled probes were measured.

TABLE 3

| Probe | 5' Fluorophore | Probe Sequence | 3' Quencher |
|---|---|---|---|
| Probe 1 | FAM | ATG CCC TCC CCC ATG CCA TCC TGC GT (SEQ ID NO: 1) | BHQ1 |
| Probe 2 | | | Compound 7 |
| Probe 3 | TET | ATG CCC TCC CCC ATG CCA TCC TGC GT (SEQ ID NO: 1) | BHQ1 |
| Probe 4 | | | Compound 7 |
| Probe 5 | HEX | ATG CCC TCC CCC ATG CCA TCC TGC GT (SEQ ID NO: 1) | BHQ1 |
| Probe 6 | | | Compound 7 |

Figure 3:
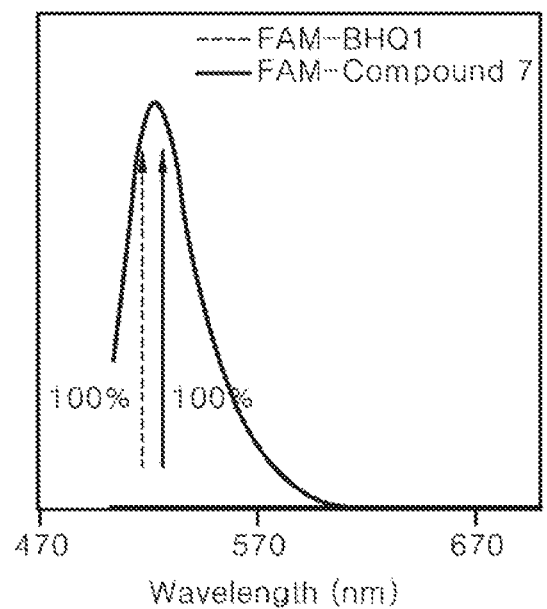
Figure 4:
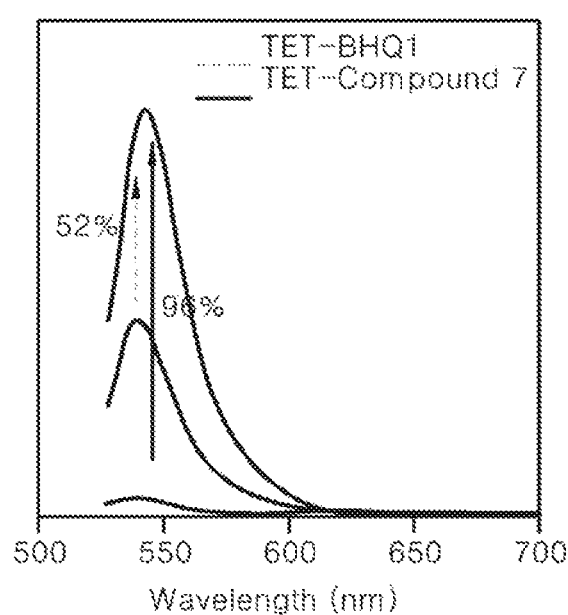
Figure 5:
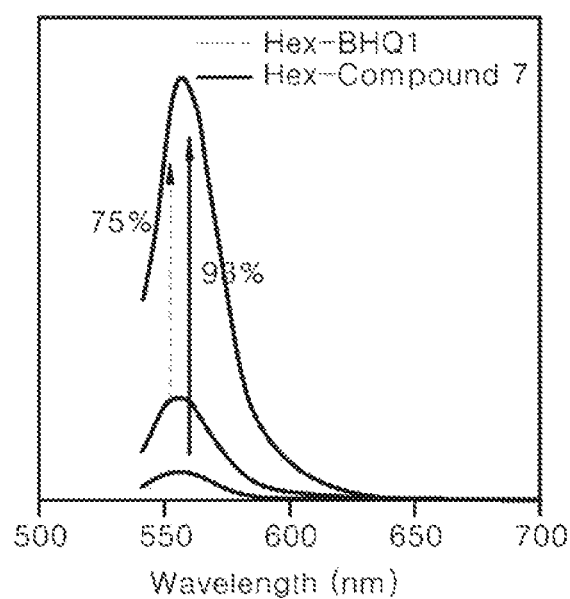

In FIG. 3 to FIG. 5, the black line indicates the fluorescence value of each fluorophore and BHQ1 in the probe state, the red line represents the fluorescence value of each fluorophore and compound 7 in the probe state, and the gray line shows the fluorescence value of the fluorophore when the probe is decomposed.

Referring to FIG. 3, which shows the quenching efficiency of a double-labeled probe (Probe 1) composed of each FAM and BHQ1 attached to the ends of a nucleotide sequence represented by SEQ ID NO: 1, and a double-labeled probe (Probe 2) composed of each FAM and compound 7 attached to the ends of the nucleotide sequence represented by SEQ ID NO: 1, it can be confirmed that the quenching properties of BHQ1 of Probe 1 and Compound of Probe 2 are similar with each other.

Meanwhile, FIG. 4 shows the quenching efficiency of a double-labeled probe (Probe 3) in which the fluorophore and the quencher consists of TET and BHQ1 are attached to the 5' end and 3' end of the nucleotide sequence represented by SEQ ID NO: 1, respectively, and a double-labeled probe (Probe 4) in which the fluorophore and the quencher consists of TET and Compound 7 are attached to the 5' end and 3' end of the nucleotide sequence represented by SEQ ID NO: 1, respectively; while FIG. 5 shows the quenching efficiency of a double-labeled probe (Probe 5) in which the fluorophore and the quencher consists of HEX and BHQ1 are attached to the 5' end and 3' end of the nucleotide sequence represented by SEQ ID NO: 1, respectively, and a double-labeled probe (Probe 6) in which consists of HEX and Compound 7 are attached to the 5' end and 3' end of the nucleotide sequence represented by SEQ ID NO: 1, respectively. Referring to FIGS. 4 and 5, it can be confirmed that the quenching properties of Compound 7 are 44% (TET) and 18% (HEX) higher than BHQ 1.

Figure 6:
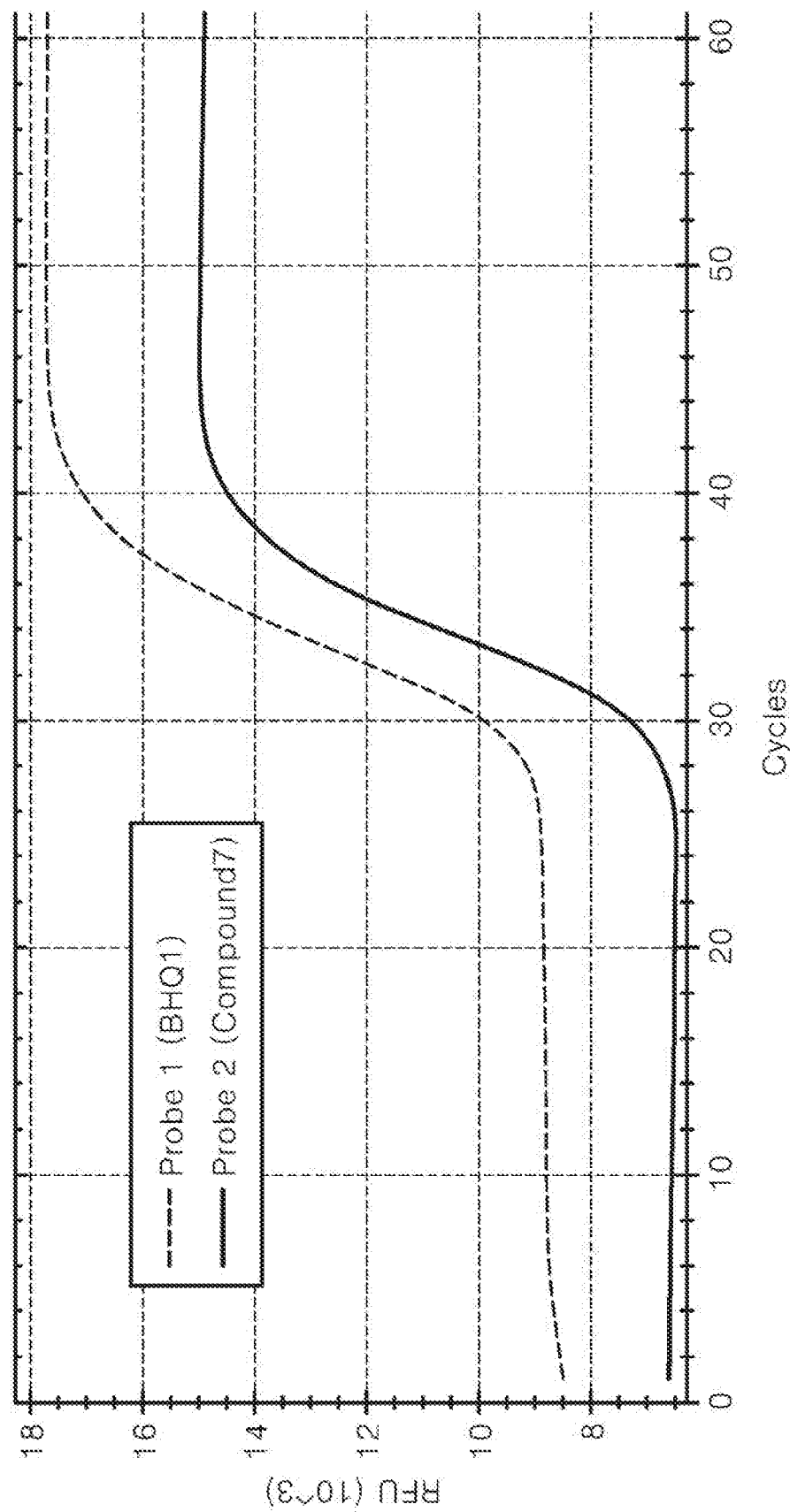

Referring to FIG. 6, a human DNA (20 ng), primer (0.5 µM each), and dual labeled probes (0.2 µM) were mixed and amplified using CFX96 real time PCR. THE probe using Compound 7 shows a lower background signal than the probe with BHQ1. It will be apparent to a person who has an ordinary knowledge in the art that various modifications and corrections by addition, change or deletion of the constitutive components may be made without departing from the spirit of the invention as set forth in the appended claims. The above modifications and corrections are also within the scope of the present invention.

What is claimed is:

1. A quencher represented by the following formula 1 or 2:

[Formula 1]

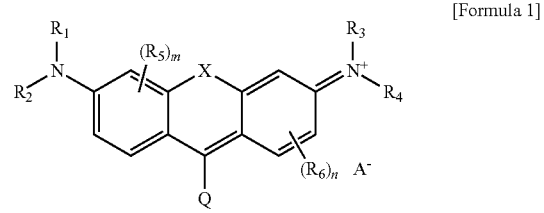

-continued

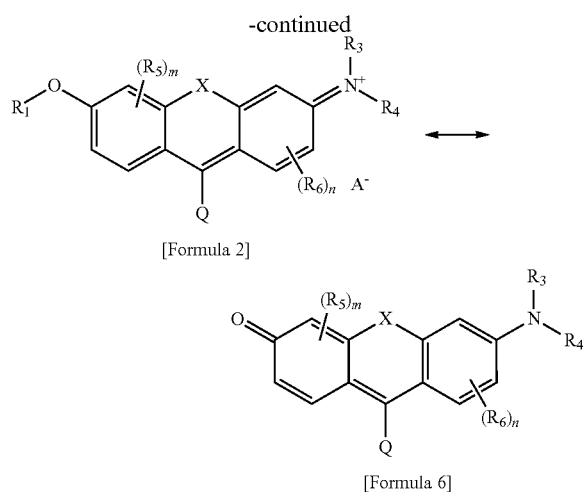

[Formula 2]

[Formula 6]

wherein Q is represented by Formula (3)

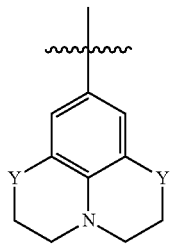

or Formula (4)

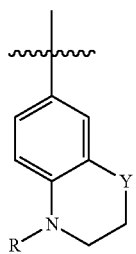

$R_1$, $R_2$, $R_3$, $R_4$, $R_5$, $R_6$ and R are each independently selected from hydrogen, deuterium, electron donating group and electron withdrawing group, m and n are each independently an integer of 0 to 3, X is O, S, $CR_7R_8$ or $SiR_7R_8$, Y is O or S, $R_7$ and $R_8$ are each independently selected from substituted or unsubstituted $C_1$-$C_{40}$ alkyl, substituted or unsubstituted $C_1$-$C_{40}$ heteroalkyl including at least one heteroatom, substituted or unsubstituted aryl, and substituted or unsubstituted heteroaryl, or are combined with each other to form a ring, and at least one of $R_1$, $R_2$, $R_3$ and $R_4$ is a functional group selected from a carboxyl, a carboxyl derivative, a hydroxyl, a haloalkyl, a nucleophile, an aldehyde, a ketone, a sulfonyl halide, a thiol, an amine, a sulfhydryl, an alkene, an epoxide and a phospoamidite, or is a reactive group capable of covalently bonding to the functional group.

2. The quencher according to claim 1, wherein $R_1$ and $R_2$ are bonded to each other to form a substituted or unsubstituted ring.

3. The quencher according to claim 1, wherein at least one selected from $R_1$ and $R_2$ are bonded with adjacent $R_5$ to form a substituted or unsubstituted ring.

4. The quencher according to claim 1, wherein $R_3$ and $R_4$ are bonded to each other to form a substituted or unsubstituted ring.

5. The quencher according to claim 1, wherein at least one selected from $R_3$ and $R_4$ are bonded with adjacent $R_6$ to form a substituted or unsubstituted ring.

6. The quencher according to claim 1, wherein the reactive group is selected from carboxyl, hydroxyl, haloalkyl, nucleophile, aldehyde, ketone, sulfonyl halide, thiol, amine, alkene, epoxide and phosphoramidite, and is protected with a protecting group.

7. An oligonucleotide comprising: a quencher according to claim 1; a minor groove binder (MGB); and a fluorophore.

8. The oligonucleotide according to claim 7, wherein the fluorophore is at least one selected from coumarin, cyanine, BODIPY, flocaine, rhodamine, pyrene, carbopyronine, oxazine, xanthine, thioxanthene, acridine and derivatives thereof.

9. A composition for detecting a nucleic acid comprising the oligonucleotide according to claim 7.

10. A support for detecting a nucleic acid comprising: a quencher according to claim 1; a support; and a linker connecting the quencher and the support.

11. The support for detecting a nucleic acid according to claim 10, wherein the support is a glass, a cellulose, a nylon, an acrylamide a gel, a dextran, a polystyrene or a resin.

12. The support for detecting a nucleic acid according to claim 10, wherein the linker is selected from substituted or unsubstituted $C_1$-$C_{30}$ alkyl, substituted or unsubstituted $C_2$-$C_{30}$ heteroalkyl having at least one heteroatom, substituted or unsubstituted $C_6$-$C_{30}$ aryl, and substituted or unsubstituted $C_3$-$C_{30}$ heteroaryl.

13. A method for detecting a nucleic acid, comprising the steps of:
(a) preparing a reaction mixture comprising a target nucleic acid, a reagent necessary to amplify the target nucleic acid and an oligonucleotide according to claim 7;
(b) amplifying the target nucleic acid in the reaction mixture by a polymerase chain reaction; and
(c) measuring fluorescence intensity of the reaction mixture.

14. The method for detecting a nucleic acid according to claim 13, wherein the step (b) comprises:
(b-1) elongating the oligonucleotide hybridized to the target nucleic acid by a polymerase;
(b-2) separating the quencher and the fluorophore of the oligonucleotide from the target nucleic acid by an exonuclease activity of the polymerase; and
(b-3) emitting fluorescence of the fluorophore which is cleaved from the quencher.

15. The method for detecting a nucleic acid according to claim 13, further comprising the step (d) of measuring amplification amount of the target nucleic acid from the fluorescence intensity measured in the step (c).

* * * * *

SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: Nucleotide linker linking a 5' fluorophore and a 3' quencher

<400> SEQUENCE: 1
atgccctccc ccatgccatc ctgcgt                                          26